(12) United States Patent
Minas

(10) Patent No.: US 12,366,524 B2
(45) Date of Patent: Jul. 22, 2025

(54) FRUIT MATURITY AND QUALITY SCANNING

(71) Applicant: Colorado State University Research Foundation, Fort Collins, CO (US)

(72) Inventor: Ioannis Minas, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 147 days.

(21) Appl. No.: 18/178,671

(22) Filed: Mar. 6, 2023

(65) Prior Publication Data

US 2024/0302272 A1    Sep. 12, 2024

Related U.S. Application Data

(63) Continuation of application No. PCT/US2021/050669, filed on Sep. 16, 2021.
(Continued)

(51) Int. Cl.
*G01N 21/3563* (2014.01)
*G01N 21/3581* (2014.01)

(52) U.S. Cl.
CPC ..... *G01N 21/3563* (2013.01); *G01N 21/3581* (2013.01); *G01N 2201/0221* (2013.01)

(58) Field of Classification Search
CPC .......... G01N 21/3563; G01N 21/3581; G01N 2201/0221; G01N 21/31; G01N 21/359
See application file for complete search history.

(56) References Cited

U.S. PATENT DOCUMENTS

2018/0313804 A1\* 11/2018 Rogel-Castillo ..... G01N 33/025
2020/0100445 A1\* 4/2020 Saba ..................... G06F 7/00

FOREIGN PATENT DOCUMENTS

WO   WO-2021010817 A1 \*  1/2021
WO   WO-2022060983 A1 \*  3/2022

OTHER PUBLICATIONS

Minas et al., Accurate non-destructive prediction of peach fruit internal quality and physiological maturity with a single scan using near infrared spectroscopy, Jul. 25, 2020 Food Chemistry vol. 335, p. 1-13. (Year: 2021).\*

(Continued)

*Primary Examiner* — Edwin C Gunberg
(74) *Attorney, Agent, or Firm* — McKee, Voorhees & Sease, PLC

(57) ABSTRACT

The true impact of preharvest factors such as crop load, canopy position, cultivar and rootstock on peach internal quality can be determined using multivariate visible light radiation (Vis) and near infrared spectroscopy (NIRS) prediction models to non-destructively assess peach internal quality (dry matter content, DMC; soluble solids concentration, SSC) and maturity (index of absorbance difference, $I_{AD}$). A novel crop load×fruit developmental stage protocol allowed accurate multivariate Vis-NIRS-based prediction models development for three major yellow fleshed peach typologies (fully red over-colored, early-ripening bi-colored and late-ripening bi-colored) to non-destructively assess peach internal quality (DMC and SSC) and maturity ($I_{AD}$) with a single scan during fruit growth and development in the field. The impact of preharvest factors such as crop load and canopy position on peach quality and maturity can be evaluated across a variety of peach cultivars using this novel technology.

18 Claims, 27 Drawing Sheets

Related U.S. Application Data

(60) Provisional application No. 63/079,210, filed on Sep. 16, 2020.

(56) References Cited

OTHER PUBLICATIONS

Escribano et al., Non-destructive prediction of soluble solids and dry matter content using NIR spectroscopy and its relationship with sensory quality in sweet cherries, 2017, Postharvest Biology and Technology, vol. 128 pp. 112-120. (Year: 2017).*

Scalisi et al., Application of visible/NIR spectroscopy for theestimation of soluble solids, dry matter and flesh firmness in stone fruits, Sep. 25, 2020, J.Sci. Food. Argi, vol. 101, pp. 2100-2107. (Year: 2020).*

Ziosi et al., "A new index based on vis spectroscopy to characterize the progression of ripening in peach fruit", Postharvest Biology and Technology, vol. 49, pp. 319-329, 2008.

Zwieniecki et al., "A potential role for xylem-phloem interactions in the hydraulic architecture of trees: effects of phloem girdling on xylem hydraulic conductance", Tree Physiology, vol. 24, pp. 911-917, 2004.

Anthony et al., "Early metabolic priming under differing carbon sufficiency conditions influences peach fruit quality development", Plant Physiology and Biochemistry, vol. 157, pp. 416-431, 2020.

Bobelyn et al., "Postharvest quality of apple predicted by NIR-spectroscopy: Study of the effect of biological variability on spectra and model performance", Postharvest Biology and Technology, vol. 55, pp. 133-143, 2010.

Boldingh et al., "Seasonal Concentrations of Non-Structural Carbohydrates of Five Actinidia Species in Fruit, Leaf and Fine Root Tissue", Annals of Botany, vol. 85, pp. 469-476, 2000.

Bruhn et al., "Consumer Perceptions of Quality Apricots, Cantaloupes, Peaches, Pears, Strawberries, and Tomatoes", Journal of Food Quality, vol. 14, pp. 187-195, 1991.

Bureau et al., "Rapid and non-destructive analysis of apricot fruit quality using FT-near-infrared spectroscopy", Food Chemistry, vol. 113, pp. 1323-1328, 2009.

Byrne, David H., "Trends in Stone Fruit Cultivar Development", HortTechnology, vol. 15(3), pp. 494-500, Jul. 2005.

Chalmers et al., "Photosynthesis in Relation to Growth and Distribution of Fruit in Peach Trees", Aust. J. Plant Physiol., vol. 2, pp. 635-645, 1975.

Costa et al., "Use of Vis/NIR Spectroscopy to Assess Fruit Ripening Stage and Improve Management in Post-Harvest Chain", Global Science Books, Fresh Produce 3, (Special Issue 1), pp. 35-41, 2009.

Crisosto, Carlos H., "Stone fruit maturity indices: a descriptive review", Postharvest News and Information, vol. 5, No. 6, pp. 65N-68N, 1994.

Crisosto, Carlos H., "How do we Increase Peach Consumption?", International Society for Horticultural Science, 5 pages, 2001.

Crisosto et al., "Relationship between ripe soluble solids concentration (RSSC) and consumer acceptance of high and low acid melting flesh peach and nectarine (Prunus persica (L.) Batsch) cultivars", Postharvest Biology and Technology, vol. 38, pp. 239-246, 2005.

Crisosto et al., "Preharvest Factors Affecting Peach Quality", The Peach: Botany, Production and Uses, Ch 20, pp. 536-549, 2009.

Cubeddu et al., "Nondestructive quantification of chemical and physical properties of fruits by time-resolved reflectance spectroscopy in the wavelength range 650-1000 nm", Applied Optics, vol. 40, No. 4, pp. 538-543, Feb. 1, 2001.

DeJong et al., "Seasonal patterns of reproductive and vegetative sink activity in early and late maturing peach (Prunus persica) cultivars", Physiol. Plantarum, vol. 71, pp. 83-88, 1987.

Diago et al., "Development and Validation of a New Methodology to Assess the Vineyard water Status by On-the-Go Near Infrared Spectroscopy", Frontiers in Plant Science, vol. 9, Article 59, 13 pages, Jan. 2018.

Donis-Gonzalez et al., "Performance Evaluation of Two Commercially Available Portable Spectrometers to Non-Invasively Determine Table Grape and Peach Quality Attributes", Agronomy, vol. 10, 16 pages, 2020.

Escribano et al., "Non-destructive prediction of soluble solids and dry matter content using NIR spectroscopy and its relationship with sensory quality in sweet cherries", Postharvest Biology and Technology, vol. 128, pp. 112-120, 2017.

Giovannoni et al., "The Epigenome and Transcriptional Dynamics of Fruit Ripening", Annu. Rev. Plant Biol., vol. 68, pp. 61-84, 2017.

Goncalves et al., "On-tree maturity control of peach cultivars: Comparison between destructive and nondestructive harvest indices", Scientia Horticulturae, vol. 209, pp. 293-299, 2016.

Grassi et al., "Advances in NIR spectroscopy applied to process analytical technology in food industries", Current Opinion in Food Science, vol. 22, 5 pages, 2018.

Grossman et al., "Maximum Vegetative Growth Potential and Seasonal Patterns of Resource Dynamics during Peach Growth", Annals of Botany, vol. 76, pp. 473-482, 1995.

Harker et al., "Sensory interpretation of instrumental measurements 2: sweet and acid taste of apple fruit", Postharvest Biology and Technology, vol. 24, pp. 241-250, 2002.

Iglesias et al., "Differential effect of cultivar and harvest date on nectarine colour, quality and consumer acceptance", Scientia Horticulturae, vol. 120, pp. 41-50, 2009.

Kumar et al., "Postharvest performance of apple phenotypes predicted by near-infrared (NIR) spectral analysis", Postharvest Biology and Technology, vol. 100, pp. 16-22, 2015.

Lan et al., "A new application of NIR spectroscopy to describe and predict purees quality 2 from the non-destructive apple measurements", Food Chemistry, vol. 310, 39 pages, Apr. 25, 2020.

Li et al., "Quantitative prediction of post storage 'Hayward' kiwifruit attributes using at harvest Vis-NIR spectroscopy", Journal of Food Engineering, vol. 202, pp. 46-55, Jun. 2017.

Liverani et al., "Superior Taste and Keeping Quality are Steady Goals of the Peach Breeding Activity at CRA-FRF, Italy", Acta Horticulturae, No. 1084, pp. 179-185, 2015.

Louw et al., "Robust prediction models for quality parameters in Japanese plums (Prunus salicina L.) using NIR spectroscopy", Postharvest Biology and Technology, vol. 58, pp. 176-184, 2010.

Lurie et al., "Chilling injury in peach and nectarine", Postharvest Biology and Technology, vol. 37, pp. 195-208, 2005.

Marini et al., "Crop Load Management", The Peach: Botany, Production and Uses, Ch 12, pp. 289-302, 2008.

Marques et al., "Rapid and non-destructive determination of quality parameters in the 'Tommy Atkins' mango using a novel handheld near infrared spectrometer", Food Chemistry, vol. 197, pp. 1207-1214, 2016.

Minas et al., "Postharvest handling of plums (Prunus salicina Lindl.) at 10 ° C. to save energy and preserve fruit quality using an innovative application system of 1-MCP", Postharvest Biology and Technology, vol. 76, pp. 1-9 2013.

Minas et al., "Discovery of non-climacteric and suppressed climacteric bud sport mutations originating from a climacteric Japanese plum cultivar (Prunus salicina Lindl.)", Frontiers in Plant Science, vol. 6, Article 316, 16 pages, May 2015.

Minas et al., "Ozone-induced inhibition of kiwifruit ripening is amplified by 1-methylcyclopropene and reversed by exogenous ethylene", BMC Plant Biology, vol. 18, 19 pages, 2018.

Minas et al., "Environmental and orchard bases of peach fruit quality", Scientia Horticulturae, vol. 235, pp. 307-322, 2018.

Minas et al., "Accurate non-destructive prediction of peach fruit internal quality and physiological maturity with a single scan using near infrared spectroscopy", Food Chemistry, vol. 335, 13 pages, 2021.

Monti et al., "Metabolic profiling of a range of peach fruit varieties reveals high metabolic diversity and commonalities and differences during ripening", Food Chemistry, vol. 190, pp. 879-888, 2016.

Nascimento et al., "Robust PLS models for soluble solids content and firmness determination in low chilling peach using near-infrared spectroscopy (NIR)", Postharvest Biology and Technology, vol. 111, pp. 345-351, 2016.

(56) References Cited

OTHER PUBLICATIONS

Nicolai et al., "Nondestructive Measurement of Fruit and Vegetable Quality", Annu. Rev. Food Sci. Technol., vol. 5, pp. 285-312, 2014.
Okie et al., "Fresh Market Cultivar Development", The Peach: Botany, Production and Uses, Ch 6, pp. 139-174, 2008.
Palmer et al., "Fruit dry matter concentration: a new quality metric for apples", Journal Sci. Food Agric., vol. 90, pp. 2586-2594, 2010.
Sanchez et al., "Testing of a local approach for the prediction of quality parameters in intact nectarines using a portable NIRS instrument", Postharvest Biology and Technology, vol. 60, pp. 130-135, 2011.
Sans et al., "Determination of chemical properties in 'calcot' (*Allium cepa* L.) by near infrared spectroscopy and multivariate calibration", Food Chemistry, vol. 262, pp. 178-183, 2018.
Slaughter et al., "Nondestructive determination of total and soluble solids in fresh prune using near infrared spectroscopy", Postharvest Biology and Technology, vol. 28, pp. 437-444, 2003.
Spadoni et al., "An innovative use of DA-meter for peach fruit postharvest management", Scientia Horticulturae, vol. 201, pp. 140-144, 2016.
Subedi et al., "Assessment of avocado fruit dry matter content using portable near infrared spectroscopy: Method and Instrumentation optimisation", Postharvest Biology and Technology, vol. 161, 10 pages, 2020.
Tanou et al., "Exploring priming responses involved in peach fruit acclimation to cold stress", Scientific Reports, vol. 7, 14 pages, 2017.
Theanjumpol et al., "Non-destructive identification and estimation of granulation in 'Sai Num Pung' tangerine fruit using near infrared spectroscopy and chemometrics", Postharvest Biology and Technology, vol. 153, pp. 13-20, 2019.
Wang et al., "Development of multi-cultivar models for predicting the soluble solid content and firmness of European bear (*Pyrus communis* L.) using portable vis-NIR spectroscopy", Postharvest Biology and Technology, vol. 129, pp. 143-151, 2017.
Zhang et al., "Non-destructive prediction of soluble solids and dry matter contents in eight apple cultivars using near Infrared spectroscopy", Postharvest Biology and Technology, vol. 151, pp. 111-118, 2019.

\* cited by examiner

FRUIT MATURITY AND QUALITY SCANNING

CROSS REFERENCE TO RELATED APPLICATIONS

This is a By-Pass Continuation claiming priority to PCT/US2021/050669 filed Sep. 16, 2021, which application claims priority under 35 U.S.C. § 119 to U.S. Provisional Application Ser. No. 63/079,210 filed on Sep. 16, 2020. The entire contents of these patent applications are incorporated herein by reference including, without limitation, the specification, claims, and abstract, as well as any figures, tables, or drawings thereof.

FIELD OF THE INVENTION

The present invention relates generally to a method for accurately and non-destructively predicting fruit maturity and quality and associated apparatuses having industrial applications in at least the agricultural industry. More particularly, but not exclusively, the present invention relates to the use of visible light radiation (Vis) and near infrared spectroscopy (NIRS) and a multivariate Vis-NIRS-based prediction model to evaluate internal quality and a physiological maturity of peach fruits.

BACKGROUND OF THE INVENTION

The background description provided herein gives context for the present disclosure. Work of the presently named inventors, as well as aspects of the description that may not otherwise qualify as prior art at the time of filing, are neither expressly nor impliedly admitted as prior art.

As shown in FIGS. 1-2, the United States Department of Agriculture National Agricultural Statistics Service ("USDA-NASS") reports worldwide peach [*Prunus persica* (L.) Batsch] consumption has been in decline due to poor and inconsistent quality.

This trend has not changed with the availability of numerous new cultivars with improved quality traits. See e.g., Iglesias et al., 2009, "Differential Effect of Cultivar and Harvest Date on Nectarine Colour, Quality and Consumer Acceptance", *Scientia Horticulturae*, 120(1): 41-50; Liverani et al., 2015, "Superior Taste and Keeping Quality are Steady Goals of the Peach Breeding Activity at CRA-FRF, Italy", *Acta Hortic*, 1084: 179-186; and Minas et al., 2018, "Environmental and Orchard Bases of Peach Fruit Quality", *Scientia Horticulturae*, 235: 307-322. The reduced rates of fresh peach consumption have been related with surveys that report immature, overripe and/or tasteless fruit as well as a variety of textural problems associated with interrupted ripening due to postharvest physiological disorders at the time of consumption. See Bruhn et al., 1991, "Consumer Perceptions of Quality: Apricots, Cantaloupes, Peaches, Pears, Strawberries, and Tomatoes", *Journal of Food Quality*, 14: 187-195; Byrne, "Trends in Stone Fruit Cultivar Development", *Horttechnology*, 15: 494-500 (2005); Crisosto, 2002, "How Do We Increase Peach Consumption?", *Acta Hortic*. 592: 601-605.

For increased rates of fresh peach consumption optimization of fruit quality is a necessity. Internal quality of peach fruit cannot be improved during postharvest handling, but only maintained. Thus, for significant improvement of peach consumer quality, reliable and accurate information to determine the impact of preharvest factors on fruit quality are required. Important preharvest factors include rootstock, cultivar, canopy position and crop load management as well as numerous other cultural practices adopted under different environmental conditions. To optimize the overall peach orchard quality potential across various cultivars growing in diverse conditions, the impact of preharvest parameters on peach quality and maturity is important to understand. See Crisosto et al., 2008, "The Peach: Botany, Production and Uses: Preharvest Factors Affecting Peach Quality", 536-549; and Minas et al., 2018.

Peach fruit maturity and quality cannot be fully determined by external traits, such as shape or color. Fruit flesh firmness (FF) and internal quality defined as soluble solids concentration (SSC), dry matter content (DMC) and titratable acidity (TA) are the most important indices of harvest maturity, shipping and storage potential, as well as consumer acceptance of several tree fruit crops. See Crisosto et al., 2005, "Relationship Between Ripe Soluble Solids Concentration (RSSC) and Consumer Acceptance of High and Low Acid Melting Flesh Peach and Nectarine (*Prunus persica* (L.) Batsch) Cultivars", *Postharvest Biology and Technology*, 38(3): 239-246. The traditional methodologies and apparatuses used for measuring FF, DMC, SSC and TA in fleshy fruit crops are destructive, time-consuming and labor-intensive, as shown in FIG. 10. These destructive methodologies are not friendly for large-scale data acquisition or field use to assess and understand the influence of various preharvest parameters on tree fruit maturity and internal quality in real time.

The potential for non-destructive methodology development could allow for large fruit samples in a tree canopy or in a sorting line to be analyzed quickly and repeatedly for a variety of purposes. Such as observation of quality and/or maturity evolution 'on-' and 'off-tree' throughout a season (growing or storage) to identify differences among pre- and postharvest factors. See Minas et al., 2018. This technology could potentially be adjusted to simultaneously collect data on different quality and maturity indices and allow for the development of optimized postharvest protocols on segregated fruit based on maturity and/or internal quality. See Spadoni et al., 2016, "An Innovative Use of DA-Meter for Peach Fruit Postharvest Management", *Scientia Horticulturae*, 201: 140-144; Ziosi et al., 2008 "A New Index Based on Vis Spectroscopy to Characterize the Progression of Ripening in Peach Fruit", *Postharvest Biology and Technology*, 49(3): 319-329. Among the different technologies that have been used in the recent decades NIRS is a promising non-destructive option to determine the peach fruit industry's standard quality and maturity indices. See Grassi et al., 2018, "Advances in NIR spectroscopy applied to process analytical technology in food industries", *Current Opinion in Food Science*, 22: 17-21.

Advanced sensing hardware and multivariate statistics such as partial least squares (PLS) regression analysis have been used to develop meaningful information from the analysis of the transmitted NIR radiation (780 and 2500 nm) by the fruit surface. See Nicolai et al., 2007, "Nondestructive Measurement of Fruit and Vegetable Quality by Means of NIR Spectroscopy: A Review", *Postharvest Biology and Technology*, 46(2): 99-118; and Nicolai et al., 2014, "Non-destructive Measurement of Fruit and Vegetable Quality" *Annual Review of Food Science and Technology*, 5(1): 285-312. Assessment of SSC and various internal quality traits in intact fruit including peach at harvest or postharvest have been the main focus for NIRS applications. See Escribano et al., 2017, "Non-destructive Prediction of Soluble solids and dry matter content using NIR spectroscopy and its relationship with sensory quality in sweet cherries" *Postharvest Biology and Technology*, 128: 112-120; Kumar et al., 2015, "Postharvest Performance of Apple phenotypes Predicted by Near-Infrared (NIR) Spectral Analysis", *Postharvest Biology and Technology*, 100: 16-22; Li et al., 2017, "Quantitative Prediction of Post Storage 'Hayward' Kiwifruit Attributes Using at Harvest Vis-NIR Spectroscopy", *Journal of Food Engineering*, 202: 46-55; Marques et al., 2016, "Rapid and Non-Destructive Determination of Quality Parameters in the 'Tommy Atkins' Mango Using a Novel Handheld Near Infrared Spectrometer", *Food Chemistry*, 197: 1207-1214; Sanchez et al., 2011, "Testing of a Local Approach for the Prediction of Quality Parameters in Intact Nectarines Using a Portable NIRS Instrument" *Postharvest Biology and Technology*, 60(2), 130-135; Theanjumpol et al., 2019, "Non-Destructive Identification and Estimation Of granulation in 'Sai Num Pung' Tangerine Fruit Using Near Infrared Spectroscopy and Chemometrics", *Postharvest Biology and Technology*, 153 (3), 13-20; and Zhang et al., 2019, Non-Destructive Prediction of Soluble Solids and Dry Matter Contents in Eight Apple Cultivars Using Near-Infrared Spectroscopy", *Postharvest Biology and Technology*, 151(2), 111-118.

Non-destructive NIRS assessment of DMC or SSC in fleshy fruit, so far has not provided a root mean square error of prediction (RMSEP), after independent validation, of less than 1% with an acceptable linearity ($R^2 > 0.9$). See Donis-González et al., 2020, "Performance Evaluation of Two Commercially Available Portable Spectrometers to Non-Invasively Determine Table Grape and Peach Quality Attributes", *Agronomy*, 10(1), 1-16. On the other hand, the use of NIRS for the assessment of destructed/processed fruit and vegetable crops and/or peeled fruit could provide an easier way to calibrate accurate and efficient prediction models for many qualitative parameters. See Lan et al., 2020, "A New Application of NIR Spectroscopy to Describe and Predict Purees Quality from the Non-Destructive Apple Measurements. *Food Chemistry*, 310(11), 125944; Sans et al., 2018, "Determination of Chemical Properties in 'Calgot' (*Allium cepa* L.) by Near Infrared Spectroscopy and Multivariate Calibration". *Food Chemistry*, 262(4), 178-183; Subedi & Walsh, 2020, "Assessment of Avocado Fruit Dry Matter Content Using Portable Near Infrared Spectroscopy: Method and Instrumentation Optimisation", *Postharvest Biology and Technology*, 161(11), 111078. However, there are many other quality and maturity parameters (TA, FF) as well as textural storage disorders of fresh fruit and vegetables that exist and need to be assessed as well. See Nicolai et al., 2014.

In most cases, NIRS handheld devices are 'open' for calibration for a variety of fruit species/cultivars, as well as a range of quality and maturity traits by the end user. This technology can be combined in modern sorting line applications for large-scale data collection that can improve both efficiency and real time decision making at any point in the fresh produce supply chain. See Nicolai et al., 2007; Slaughter et al., 2003, "Nondestructive Determination of Total and Soluble Solids in Fresh Prune Using Near Infrared Spectroscopy" *Postharvest Biology and Technology*, 28(3), 437-444.

Nevertheless, the need for device calibration for different quality and maturity traits across different cultivars requires highly trained personnel, and it has been met with the challenge to be broadly adopted by the tree fruit industry. Currently, non-destructive sensors with accurate prediction models of internal fruit quality (DMC, SSC, TA) and maturity (FF) parameters for numerous fruit crops, including peach, are not available yet. See Donis-González et al., 2020.

Traditional non-destructive ground color assessment to estimate peach maturity using CIE hue angle (h°) has been demonstrated to be a good index of peach maturity (peaches with ground h°<80 are mature and ready for commercial harvest). However, this index can only be used in bi-color cultivars and cannot be used in fully red over-colored cultivars due to early coverage of ground color, which leads to harvesting immature and poor-quality fruit. Visible light radiation and NIRS (Vis-NIRS) have been combined to create a non-destructive peach index that correlates with the onset of endogenous ethylene synthesis and determines fruit physiological maturity and ripening status. See Costa et al., 2009, "Use of Vis/NIR Spectroscopy to Assess Fruit Ripening Stage and Improve Management in Post-Harvest Chain" *Fresh Produce*, 3(1): 35-41; Ziosi et al., 2008. Simply, this index calculates the absorbance difference (index of absorbance difference, $I_{AD}$) between two wavelengths (670 and 720 nm) near the absorption peak of chlorophyll-$\alpha$ (A670 nm-A720 nm). A factory calibrated "closed" type handheld Vis-NIRS sensor (DA-meter, T. R. Turoni srl, Forli, Italy) can take rapid non-destructive fruit scans (i.e., $I_{AD}$ measurements) that correspond to chlorophyll concentration (ground color) a few millimeters below the skin and provide an estimate of fruit physiological maturity and consumer acceptance. See Costa et al., 2009. The $I_{AD}$ can be used to determine peach harvest time efficiently, but preliminary work is required to determine the minimum maturity thresholds for different cultivars. It is important to note that $I_{AD}$ does not correlate directly with any traditional harvest index (e.g., FF or SSC), which have also been used to define harvest stage. See Minas et al., 2018. Thus, its broad adoption by producers has been slow as it is a non-standard way to assess peach maturity. However, $I_{AD}$ is a particularly important index for newer cultivars, where harvest time is difficult to estimate due to excess red overcolor on the fruit's skin that obscures the background color, which is normally used to estimate fruit maturation. See Minas et al., 2018. Thus, there exists a need in the art for an apparatus which accurately and non-destructively predicts peach fruit internal quality and physiological maturity with a single scan using visible light radiation and near infrared spectroscopy (Vis-NIRS).

SUMMARY OF THE INVENTION

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

It is a further object, feature, and/or advantage of the present invention to create a device that can utilize the accurate non-destructive quality and maturity assessment technology and provide reliable field information with a single scan. As described herein, the use of regression statistics highlights dry matter content (DMC), soluble solids concentration (SSC), and index of absorbance difference ($I_{AD}$) can be estimated accurately with a single scan during fruit growth and development.

It is still yet a further object, feature, and/or advantage of the present invention to support growers on decisions regarding the proper harvest time.

It is still yet a further object, feature, and/or advantage of the present invention to support researchers on the evaluation of different cultural techniques, new cultivars, and rootstocks, with an aim to toward increasing orchard quality potential.

It is still yet a further object, feature, and/or advantage of the present invention to allow for accurate maturity and quality predictions in phenotypically similar cultivars to fully red over-colored and early and late bi-colored yellow fleshed cultivars. For example, individual peach cultivar models could be used to accurately predict maturity (e.g., $I_{AD}$) and quality (e.g., DMC) in similar but distinct peach cultivars sharing phenotypic characteristics and harvest time(s).

It is still yet a further object, feature, and/or advantage of the present invention to use non-destructive technologies that have enabled rapid maturity and quality assessments in near real-time, over large samples of fruit.

It is still yet a further object, feature, and/or advantage of the present invention to recognize that while improvement of peach fruit quality is impossible postharvest, optimum peach quality at harvest and after harvest is achievable through understanding the influence of preharvest and orchard factors. Crop load management, fruit position in the canopy, cultivar and rootstock are important preharvest factors to balance yield, quality, and maturation in peach.

It is thus a further object, feature, and/or advantage of the present invention to assist in the processes of collecting field data and managing orchards. For example, large-scale field validation shows heavier crop loads reduce peach quality (DMC, SSC) and delay maturity ($I_{AD}$) and upper canopy position advanced both mainly in the moderate crop loads. Improved data collection and field measurement methodologies should overcome deficiencies of traditional methodologies that are destructive and/or hard to adopt for field measurements.

It is still yet a further object, feature, and/or advantage of the present invention to develop robust individual cultivar models for peaches and other fruits. Once developed, the Vis-NIRS models should account for individual genotypes, as spectra absorption is predominantly cultivar-specific. The developed NIRS-model should further precisely and reliably assess physicochemical properties of fleshy fruit.

It is still yet a further object, feature, and/or advantage of the present invention to employ a calibration protocol that enhances Vis-NIRS adaptation across tree fruit supply chain.

The apparatus disclosed herein can be used in a wide variety of applications. For example, the disclosed methodologies and apparatuses are compatible with nearly all types of fleshy fruits, not just from *Prunus* species, including: stone fruit varieties, peaches, nectarines, apricots, and/or plums.

It is still yet a further object, feature, and/or advantage of the present invention to improve and/or optimize flavor (e.g., by mitigating bleeding), texture (e.g. by mitigating mealiness), color (e.g., by mitigating browning), hardness, and ripeness of fruits prior to consumption.

It is still yet a further object, feature, and/or advantage of the present invention to extend the timeframe in which harvested fruits can be stored and/or safely consumed.

It is still yet a further object, feature, and/or advantage of the present invention to carry out disclosed methodologies and manufacture disclosed apparatuses in a cost-effective manner such that peach farming is more profitable and the end-consumer can save money and enjoy optimum quality fruit.

It is still yet a further object, feature, and/or advantage of the present invention to increase yield and/or the peach farming capabilities of peach farms located in major peach producing countries, such as, but not limited to: China, Spain, Italy, Greece, the United States, Turkey, Iran, Chile, Argentina, and Egypt.

It is still yet a further object, feature, and/or advantage of the present invention to increase yield and/or the peach farming capabilities of peach farms located in major peach producing U.S. states, such as, but not limited to: California, South Carolina, Georgia, New Jersey, Pennsylvania, Washington, Colorado, Michigan, Idaho, and New York.

Methods can be practiced which facilitate use, manufacture, assembly, maintenance, and repair of a hand-held spectrometer which accomplish some or all of the previously stated objectives.

Some embodiments of the present disclosure can be, but are not required to be, characterized by any one or more of the numbered paragraphs located at the end of the detailed description of the drawings.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

An artisan of ordinary skill in the art need not view, within isolated figure(s), the near infinite number of distinct permutations of features described in the following detailed description to facilitate an understanding of the present invention.

DETAILED DESCRIPTION OF THE INVENTION

The present disclosure is not to be limited to that described herein. Mechanical, electrical, chemical, procedural, and/or other changes can be made without departing from the spirit and scope of the present invention. No features shown or described are essential to permit basic operation of the present invention unless otherwise indicated.

Figure 1:
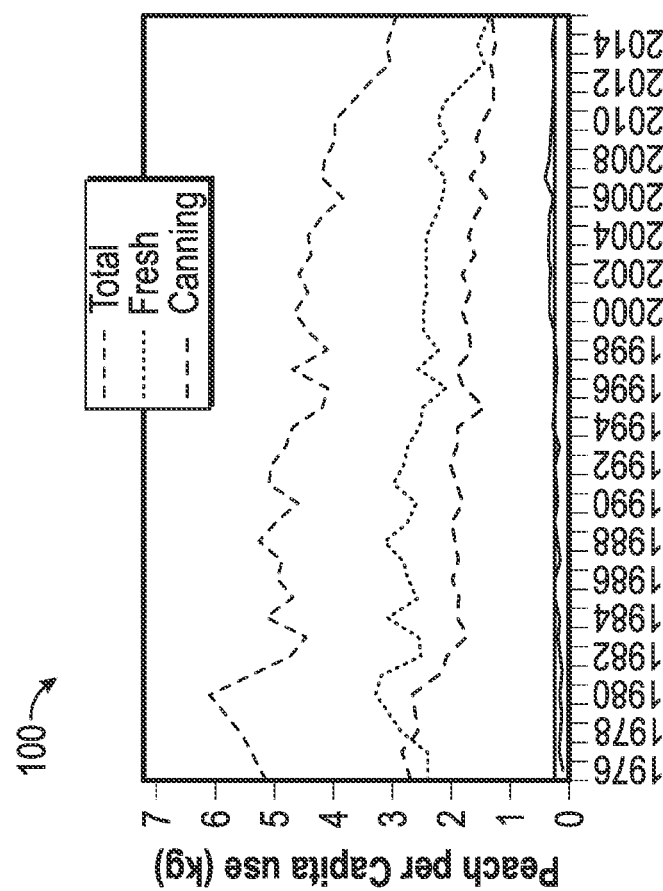
FIG. 1 is an annual time series graph spanning years 1975-2015, showing peach per capita use (in kilograms) has been steadily falling.

Referring now to the figures, FIG. 1 shows a time series graph of tracking peach per capita over time 100 from the years 1975 to 2015. Though the consumption of both fresh peaches and canning peaches has fallen, the consumption of fresh peaches has been particularly adversely affected. The peach per capita consumption in the year 2015 fell to 2.8 kilograms per person. Such a fall in demand to consume the peach has been caused in part because of poor harvest and postharvest management methods for peaches and other *Prunus* species, such as the nectarine.

Figure 2:
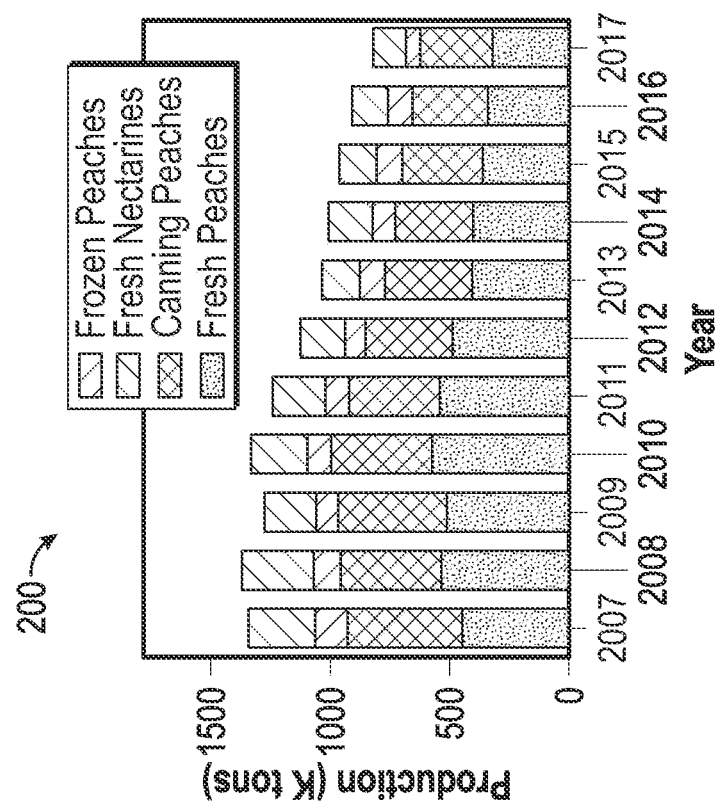
FIG. 2 charts a bar graph comparing the production of peaches and nectarines that were distributed throughout the United States during the years 2007-2017.

Labor issues also share part of the blame in the decline of the peach. Production of *Prunus* species has also fell quite significantly in the United States over recent years, as is shown in FIG. 2. More particularly, the raw production of the combination of frozen peaches, frozen nectarines, canning peaches, and fresh peaches remains below 1000 kilotons in the year 2017. Major *Prunus* species producing countries, including China, the United States, and Greece, would benefit greatly from these issues being remedied as quickly as possible.

This has led to significant research into identifying problems that plague the peach. For example, consumer surveys have revealed peach consumers regularly report that peaches at the time of consumption have too little flavor, are too hard, are too soft, never ripen, and/or are mealy. Other consumers are simply confused about the nuances of the peach. For example, about 70 stone fruit varieties released per year, however peaches and nectarines are not being sold by cultivar name. This allows for many releases per year unbeknownst to the consumer. There has also been a surge in white peaches and nectarines. Peaches and nectarines are often too acidic or not acidic enough, high in sugar types, are "red-fleshed", and/or suffer from other deficiencies.

Figure 3:
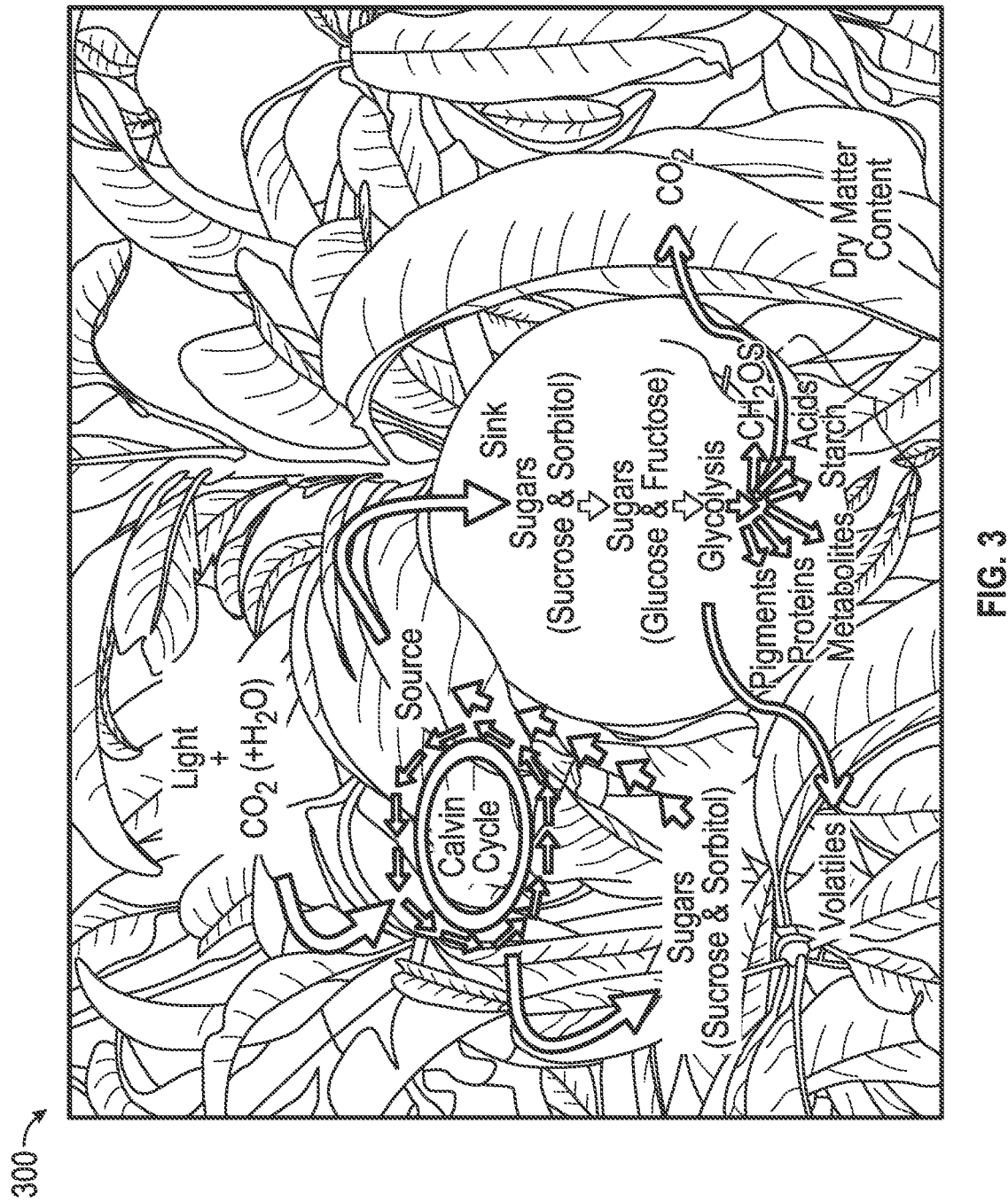
FIG. 3 models the typical processes from photosynthesis to peach fruit growth and development through sugar accumulation.

For purposes of a thorough discussion, it must be understood how fruit quality is built up in the orchard. FIG. 3 shows a growth process 300 for peaches. The peach utilizes light, carbon dioxide, and water in a subprocess known as the Calvin cycle. The Calvin cycle is a part of photosynthesis, the process plants and other autotrophs use to create nutrients from sunlight and carbon dioxide. In other words, the Calvin cycle allows peaches to turn light, carbon dioxide from the air, and water into sugar, the food autotrophs need to grow. Many other biological outputs are created during the growth of the peach, many of which (including metabolites, starch, organic acids, and the like) can be easily measured because they form part of the peach's dry matter content (DMC).

Ensuring high quality of peaches can rely on managing pre-harvest factors so as to optimize biological inputs in the aforementioned peach growth process 300.

Others have thus far focused on creating environments 400 that optimize the amount of sunlight, carbon dioxide, and water to each peach tree and/or individual peach fruits and/or by trying to harvest peaches at the correct time.

It is thus to be appreciated that the present invention, including the use of NIRS, can be implemented within such environments 400. Moreover, the present invention can even enhance the functional capabilities of said environments 400.

Figure 4:
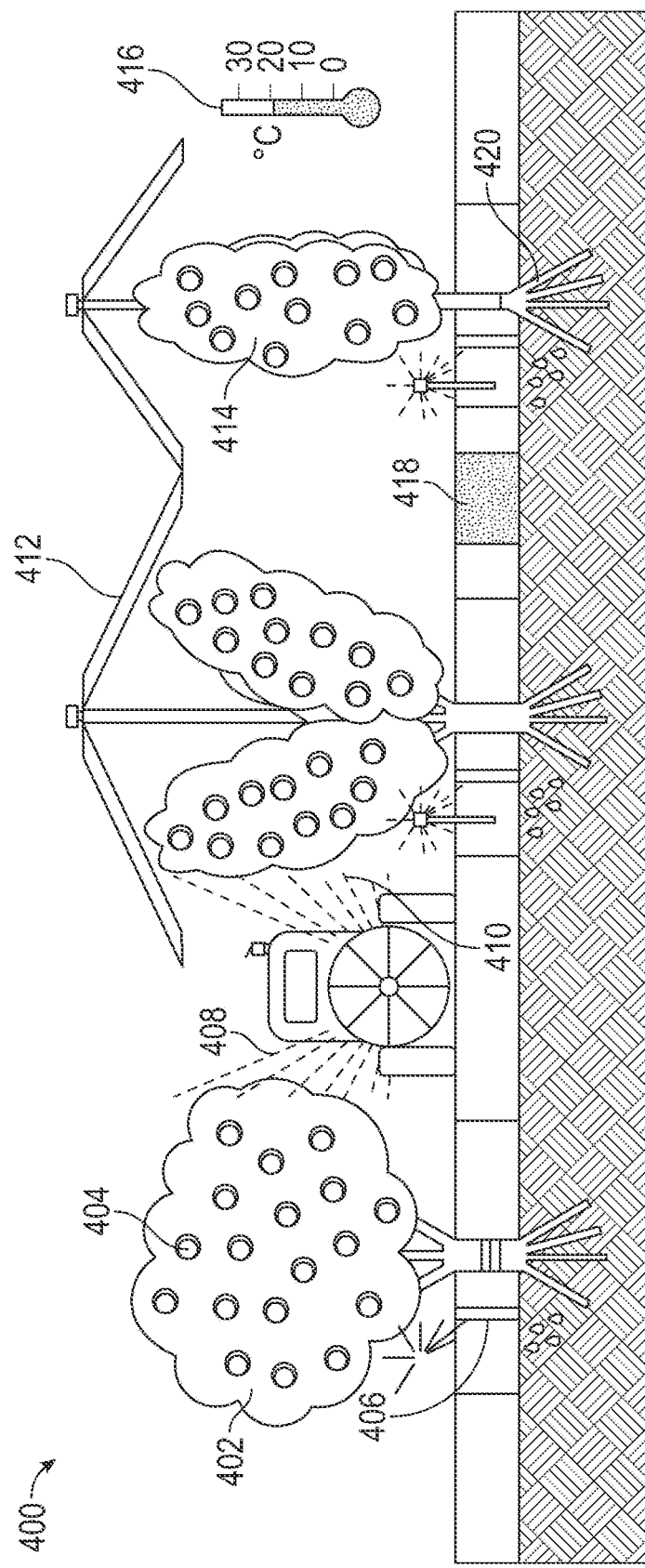
FIG. 4 illustrates a schematic view of pre-harvest factors that affect peach fruit quality.

One such example of an environment 400 is shown illustratively in FIG. 4. The environment 400 beneficially includes, but is not required to include, several different types of growth regulators that aim to facilitate growth of the peach. Such growth regulators can include thinning apparatuses 402 for managing crop loads and/or thinning times, apparatuses 404 for monitoring/managing canopy positions of fruits on a tree and/or altering canopy architectures 414 to optimize growth, irrigation systems 406, mineral nutrition (e.g., fertilizers) applicators such as foliar sprays 408, light manipulators (e.g., reflectance films 418, artificial sunlight sources, photo-selective nets 412, polarizers, and the like), growing climate monitors and/or manipulators 416 such as air quality monitoring systems and thermostats, rootstocks 420, and/or any other suitable plant growth regulators 410.

Figure 5:
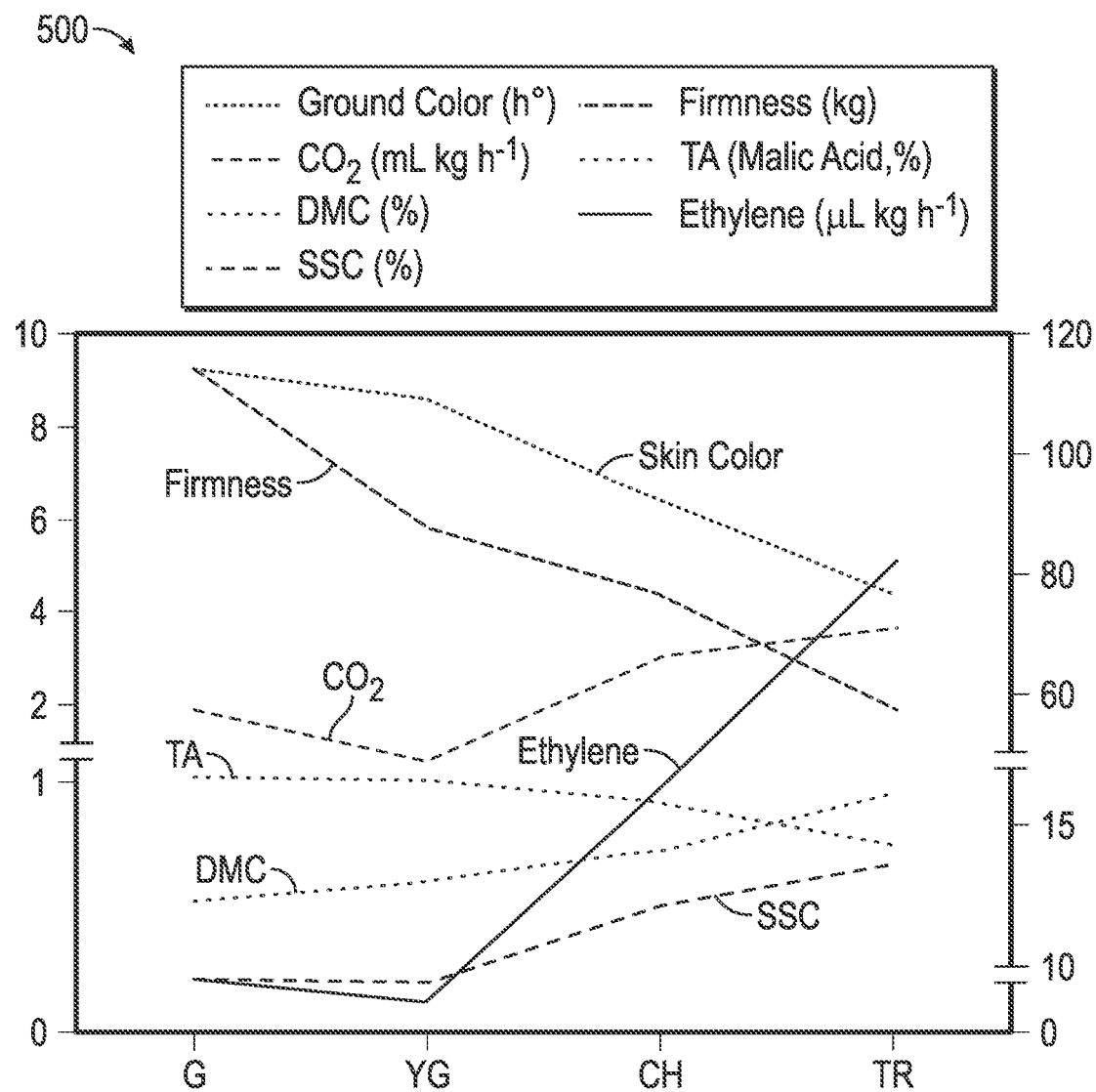
FIG. 5 graphs quality changes during 'June Gold' peach fruit development & ripening on-tree.

The quality of the peach during development and ripening on the tree will drastically change depending on the development stage. A comparison 500 of several characteristics of peaches during development and ripening on-tree is shown in FIG. 5. The peach is most firm in its earliest development stages, G and YG. As the peach approaches commercial harvest and tree-ripeness, the peach becomes less firm. The ethylene, DMC, and SSC levels in the peach increase as the peach moves from stage G to TR. The peaches outer skin color also transitions from a green color to a red color. Titratable acidity (TA) levels decrease. With this understanding, being able to measure one or more of these characteristics in a quantitative matter can inform how to continue to cultivate the peach for optimal growth or even when to harvest.

Figure 6:
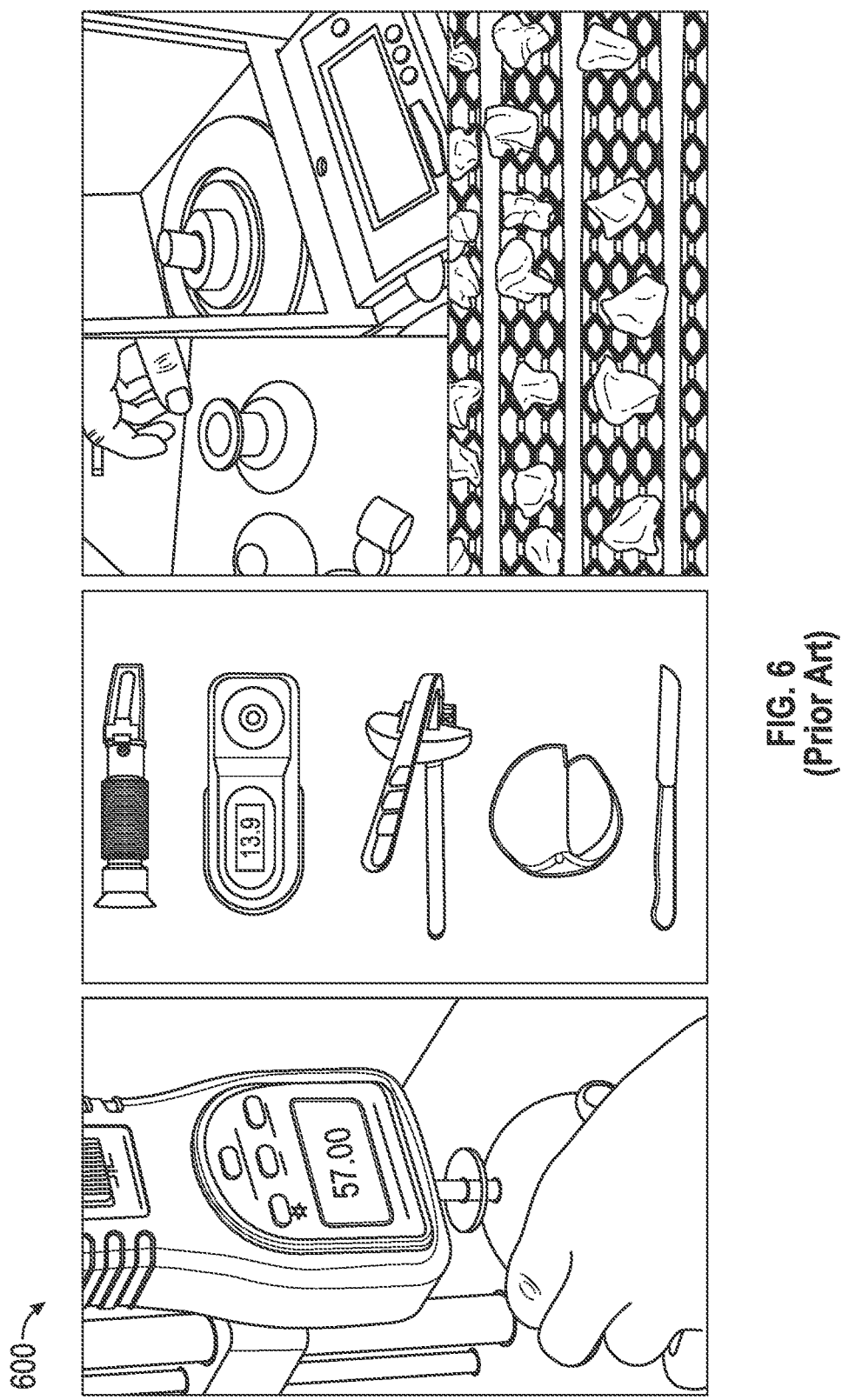
FIG. 6 exemplifies traditional methodologies and apparatuses used for measuring FF (maturity), SSC and DMC (internal quality) in fleshy fruit crops that are destructive, time-consuming and labor-intensive.

Measuring one or more of these characteristics in an efficient manner without destroying the peach is not so simple. For example, to measure many of the aforementioned characteristics, destructive methodologies and practices, were almost necessarily employed due to the lack of knowledge of other processes and/or because other processes were cost prohibitive. Destructive implementation 600 such as that shown in FIG. 6 could be used to pierce or cut into the peach to determine flesh firmness, SSC, and DMC. The peach would then not be available for later consumption. Moreover, there was no guarantee that the individual peach would be representative of all other peaches on the tree, and so quite a few peaches might have to be destroyed in order to more accurately gauge whether all of the peaches were ready for harvest.

Figure 8:
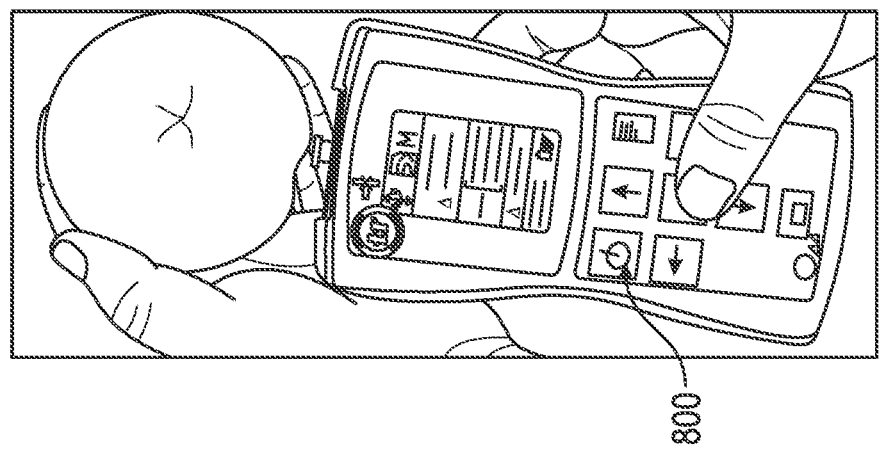
FIG. 8 exemplifies a handheld non-destructive sensor to estimate fruit maturity in the field, and in particular, shows a "closed" type DA-meter.
Figure 7:
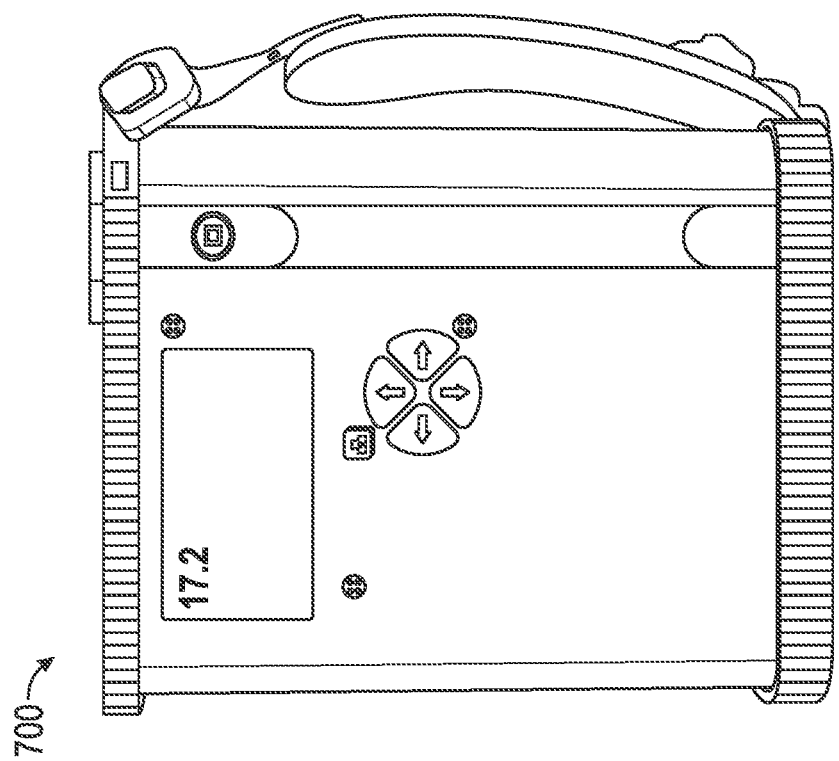
FIG. 7 exemplifies a handheld non-destructive sensor to estimate internal fruit quality in the field, and in particular, shows an "open" type produce quality meter.

It is thus important that the peaches not be destroyed when the quality and maturity of same is being evaluated. FIGS. 7-8 in particular show exemplary handheld, non-destructive sensors 700, 800 that employ Vis-NIRS.

The instrument 700 is an "open" type instrument that can be calibrated on-site. Such an instrument 700, can for example, have a range of 310-1100 nm. The instrument 700 typically includes a body that houses its components, a light source, a lens, a shutter, a display, a PC interface, a capability to automatically record data with each scan (e.g., raw data, reflectance, absorbance, first derivative absorbance), a data storage unit, and a power source. The instrument 700 can take three online measurements at the same time and display two simultaneously, and is particularly useful for estimating overall quality of peaches due to its ability to detect DMC and SSC.

The instrument 800 is a "closed" type instrument that can be calibrated at the factory. The instrument 800 relies on the use of an $I_{AD}$, such as the index of absorbance for chlorophyll content ($I_{AD}=A_{670nm}-A_{720nm}$). The instrument 800 is thus extremely useful in measuring fruit physiological maturity.

Figure 9:
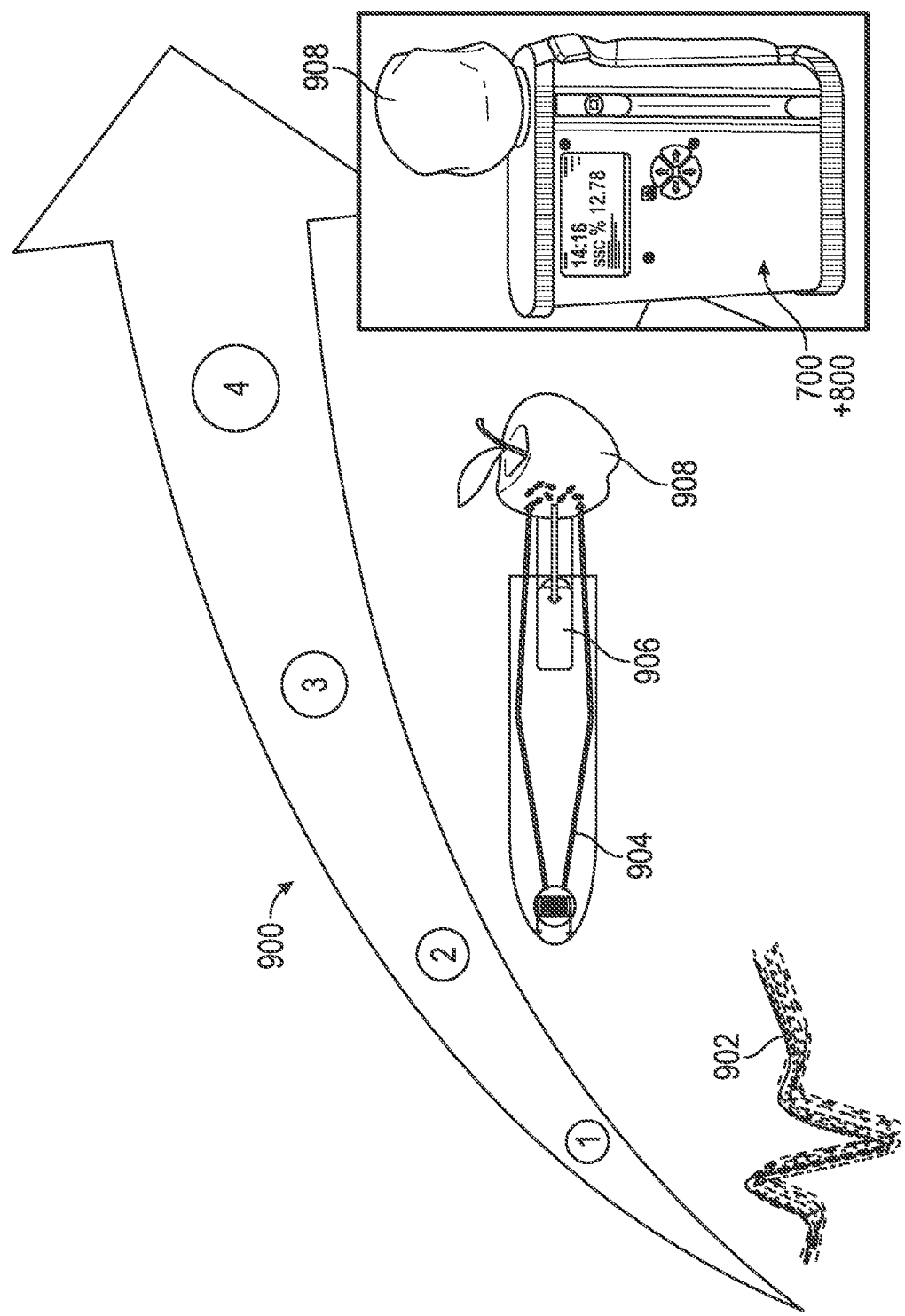
FIG. 9 illustrates a process view for measuring fruit quality non-destructively, according to some aspects of the present disclosure.

It is to be appreciated the instruments 700, 800 were advantageously combined into a single handheld instrument that can simultaneously measure overall quality of peaches (including internal characteristics) and the maturity of peaches so as to be employed in the inventive method 900 described in connection with FIG. 9.

To effectively measure fruit quality non-destructively, a first step can be to allow near infrared radiation (780-2500 nm) 902 to enter a fruit 908, such as a peach or an apple. In a second step, light 904 shall scatter and interact with the fruit tissue. Light absorbance is then measured by an intelligent spectrometer 906. The spectrometer 906, which can also include a computer processing unit capable of carrying out algorithms for creating the regression models described herein, processes and converts several raw absorbance values into one single prediction value.

The advantages of the process 900 are that the fruit 908 is not destructed, the spectrometer 906 can be used in the field, the process 900 and the spectrometer 906 together enable faster measurement, there are an increased number of sampled peaches prior to consumption, and the open portion of the system allows on-site calibration and optimization.

FIGS. 10-22 show exemplary multivariate regression models 1000 that were developed for non-destructive estimations of peach fruit internal quality and maturity for fully red over-colored cultivars (e.g., FIG. 10), early-ripening bi-colored (e.g., FIG. 21, discussed infra), and late-ripening bi-colored (see e.g., FIG. 22, discussed infra) yellow fleshed cultivars.

Figure 10:
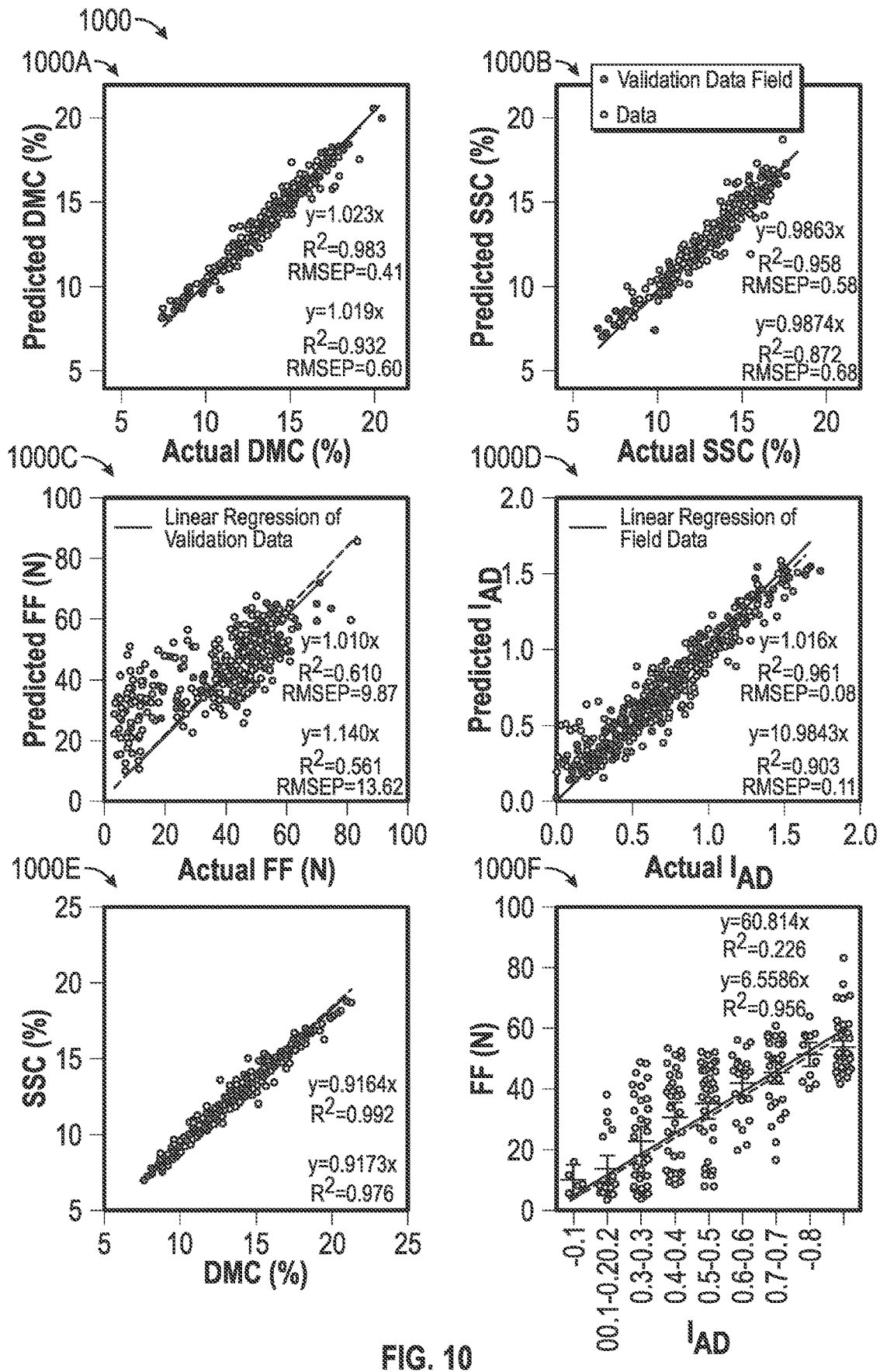
FIG. 10 employs a single scan using NIRS and a novel Vis-NIRS calibration protocol and to model several accurate non-destructive predictions of peach fruit internal quality and physiological maturity.

As shown in FIG. 10, several exemplary predicted values are plotted against actual reference values from the exact same and marked spots (validation data) for the fully red over-colored cultivar 'Sierra Rich'. In addition, predicted and reference values coming from non-marked areas from the fruit were used to evaluate the non-destructive models' performance in assessing the effect of preharvest factors on peach maturity and quality in the field (field data). Created models were tested for linearity ($R^2$) and root mean square error of prediction (RMSEP) to determine accuracy to non-destructively predict dry matter content (DMC, 1000A), soluble solids concentration (SSC, 1000B), flesh firmness (FF, 1000C) and index of absorbance difference ($I_{AD}$, 1000D), in peach fruit. Correlation coefficients of the predicted non-destructive sensor's SSC with DMC values coming from the validation and field groups of fruit are shown (1000E). Correlation coefficient of the actual $I_{AD}$ and FF values coming from the validation and field groups of fruit are shown (1000F). Validation and field data were combined to form two data sets. As will become understood, similar plotting methods are used throughout the remaining figures, which include data relating to a wide variety of cultivars. Thus, some of the remaining figures_likewise concern the fully red over-colored cultivar 'Sierra Rich' cultivar, while others concern the early ripening bi-colored cultivar 'Redhaven' (see e.g., FIG. 21), the late ripening bi-colored yellow fleshed cultivar 'Cresthaven' (see e.g., FIG. 22), and other cultivars (see e.g., FIG. 23A).

FIGS. 11-14 illustrate how various crop loads 1100 can affect fruit yield, fruit size, and the return bloom in 'Sierra Rich'. Examples of unthinned crop loads 1100A, heavy crop loads 1100B, commercial crop loads 1100C, and light crop loads 1100D are all illustrated in FIG. 11.

Figure 11:
FIG. 11 captures the effects of various crop loads on peach yield, fruit size, and return bloom.
Figure 12:
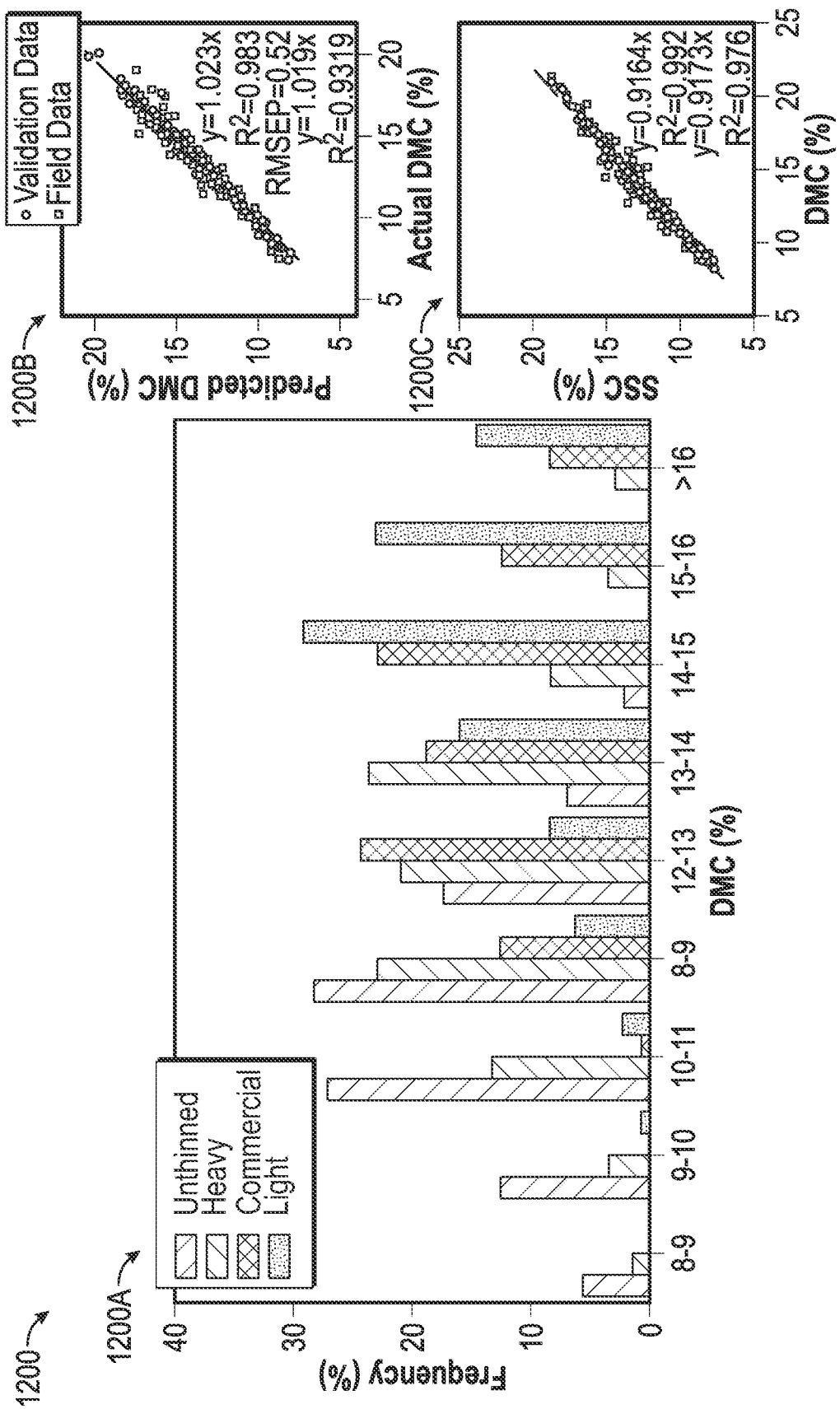
FIG. 12 exemplifies the effect of various crop loads on peach DMC at harvest as predicted by NIRS.

Exemplary effects of the various crop loads illustrated in FIG. 11 on fruit DMC at harvest as predicted by NIRS (and use of the invented NIRS-based regression models) are shown in FIG. 12. More particularly, FIG. 12 shows an exemplary comparison 1200A between frequency of crop load and DMC graphed alongside the output comparison 1200B created from using a regression model to compare predicted DMC and actual DMC. FIG. 12 also exemplifies the correlation 1200C between SSC and DMC among varying crop loads.

Figure 13:
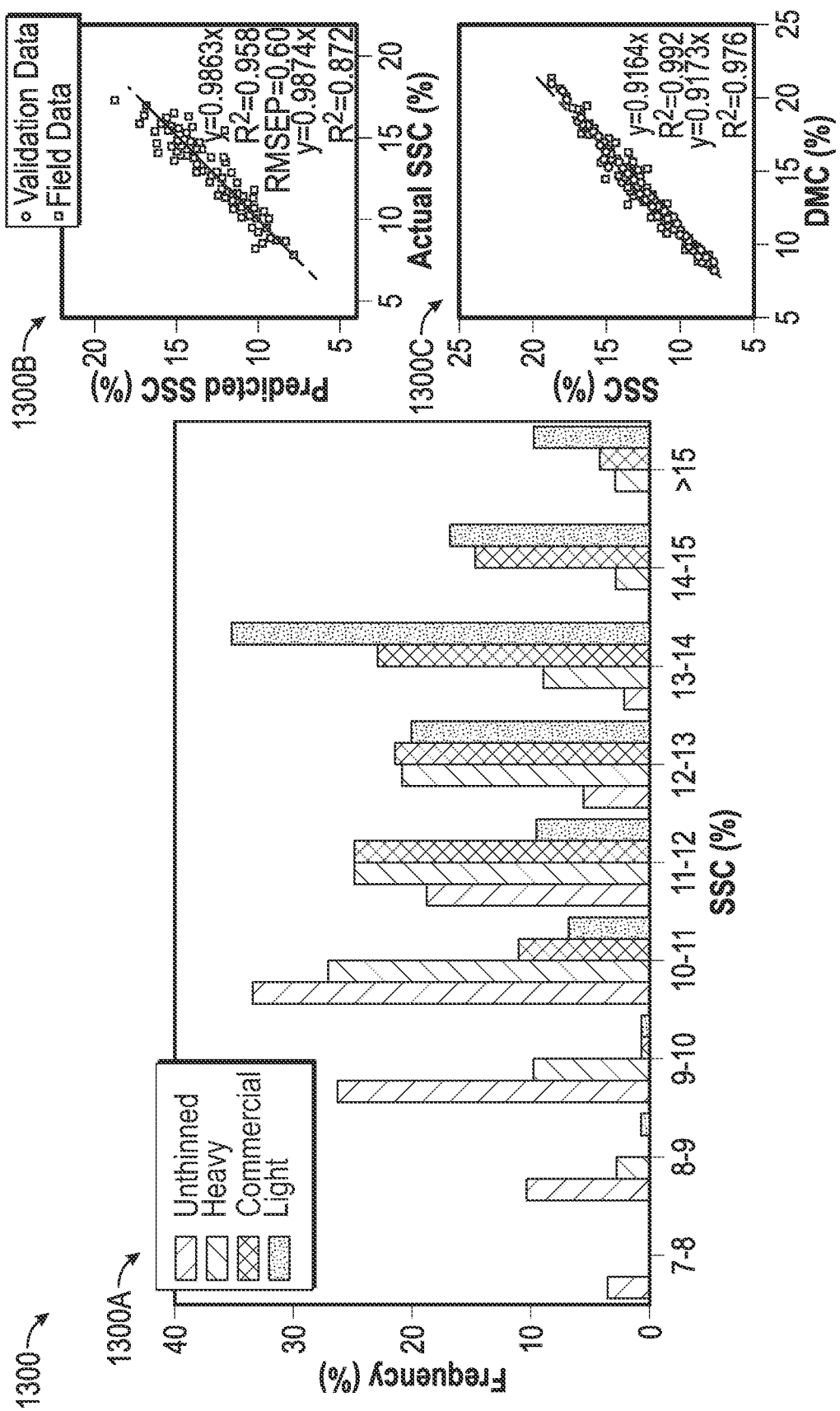
FIG. 13 exemplifies the effect of various crop loads on peach SSC at harvest as predicted by NIRS.

Exemplary effects of the various crop loads illustrated in FIG. 11 on fruit SSC at harvest as predicted by Vis-NIRS (and use of the NIRS-based regression models) are shown in FIG. 13. More particularly, FIG. 13 shows an exemplary comparison 1300A between frequency of crop load and SSC graphed alongside the output comparison 1300B created from using a regression model to compare predicted SSC and actual SSC. FIG. 13 also exemplifies the correlation 1300C between SSC and DMC among varying crop loads.

Figure 14:
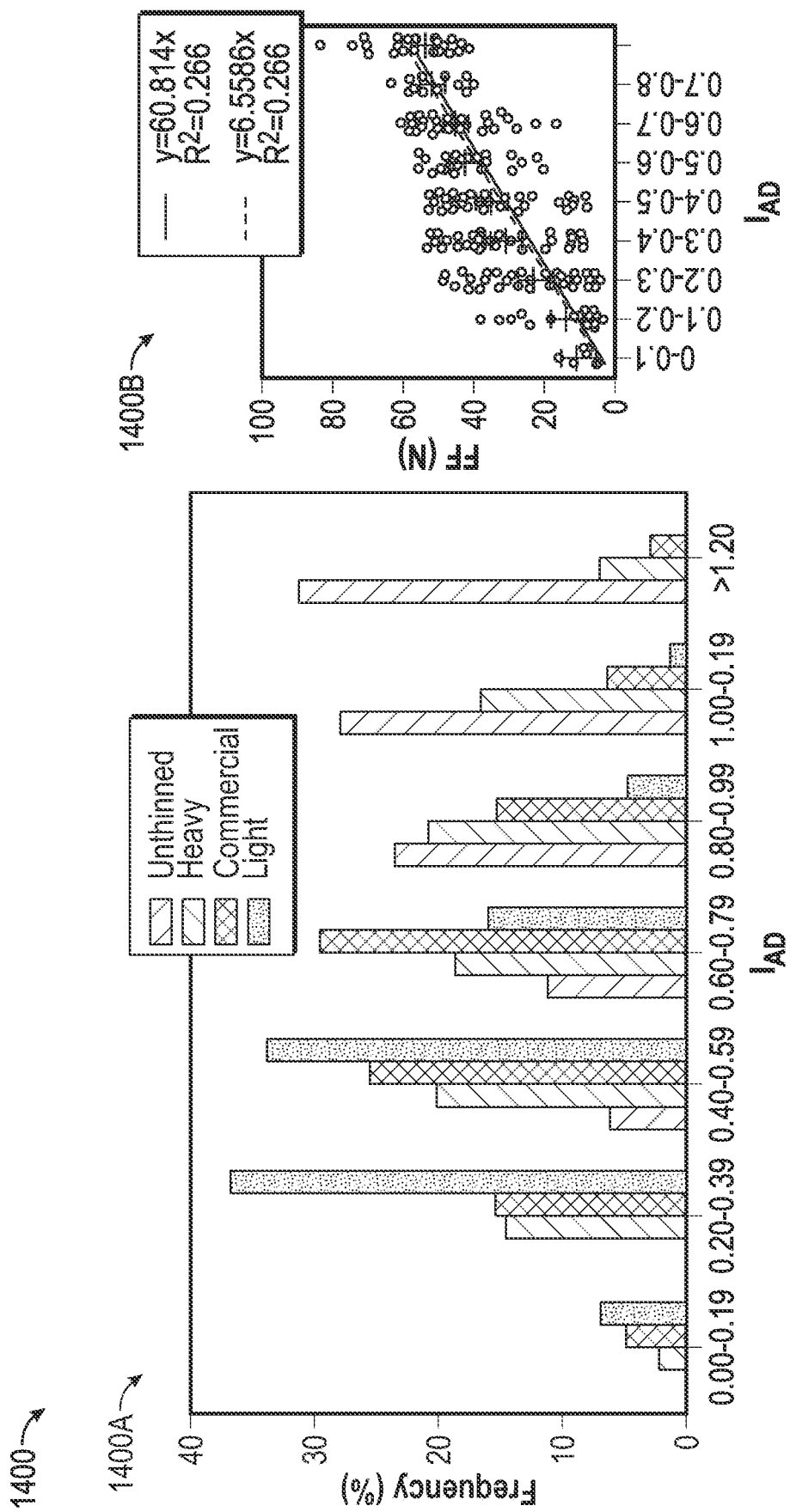
FIG. 14 exemplifies the effect of various crop loads on peach maturity at harvest assessed non-destructively with $I_{AD}$ (DA-meter).

Exemplary effects of the various crop loads illustrated in FIG. 11 on fruit maturity at harvest assessed non-destructively with $I_{AD}$ are shown in FIG. 14. More particularly, FIG. 14 shows an exemplary comparison 1400A between frequency of crop load and $I_{AD}$ graphed alongside the weak correlation 1400B created from using a regression model to compare FF and $I_{AD}$. This particular example shows that $I_{AD}$ only correlates with FF in peaches when $I_{AD}$ values are plotted in clusters, though this does describe physiological maturity better.

Figure 15:
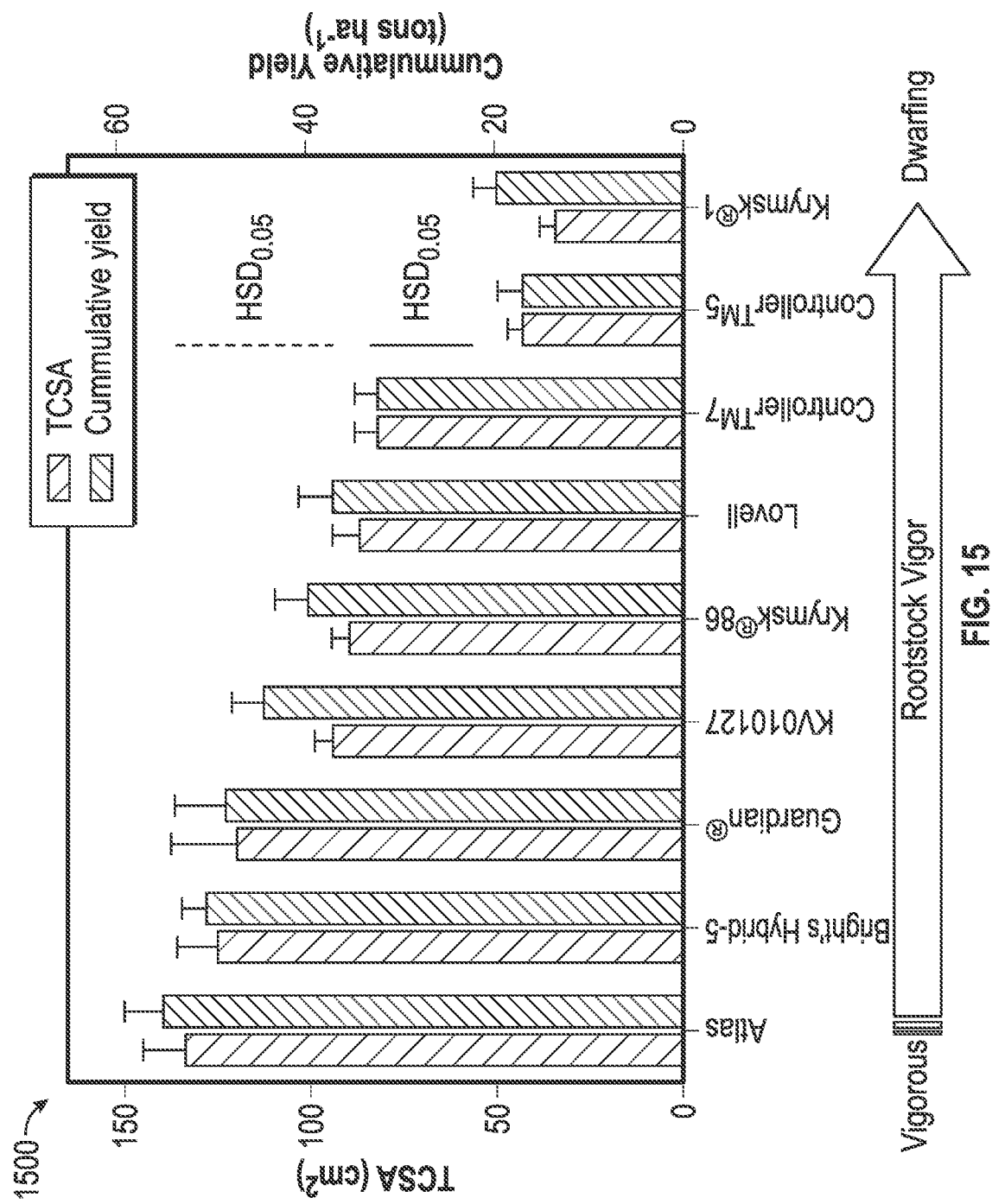
FIG. 15 exemplifies the effect of rootstock on cumulative yield per tree by comparing trunk cross-section area (TCSA) and cumulative yield.

FIG. 15 exemplifies the effect of rootstock on cumulative yield per tree by showing a comparison 1500 of trunk cross-section area ("TCSA") and cumulative yield in 'Redhaven' scions.

Figure 16:
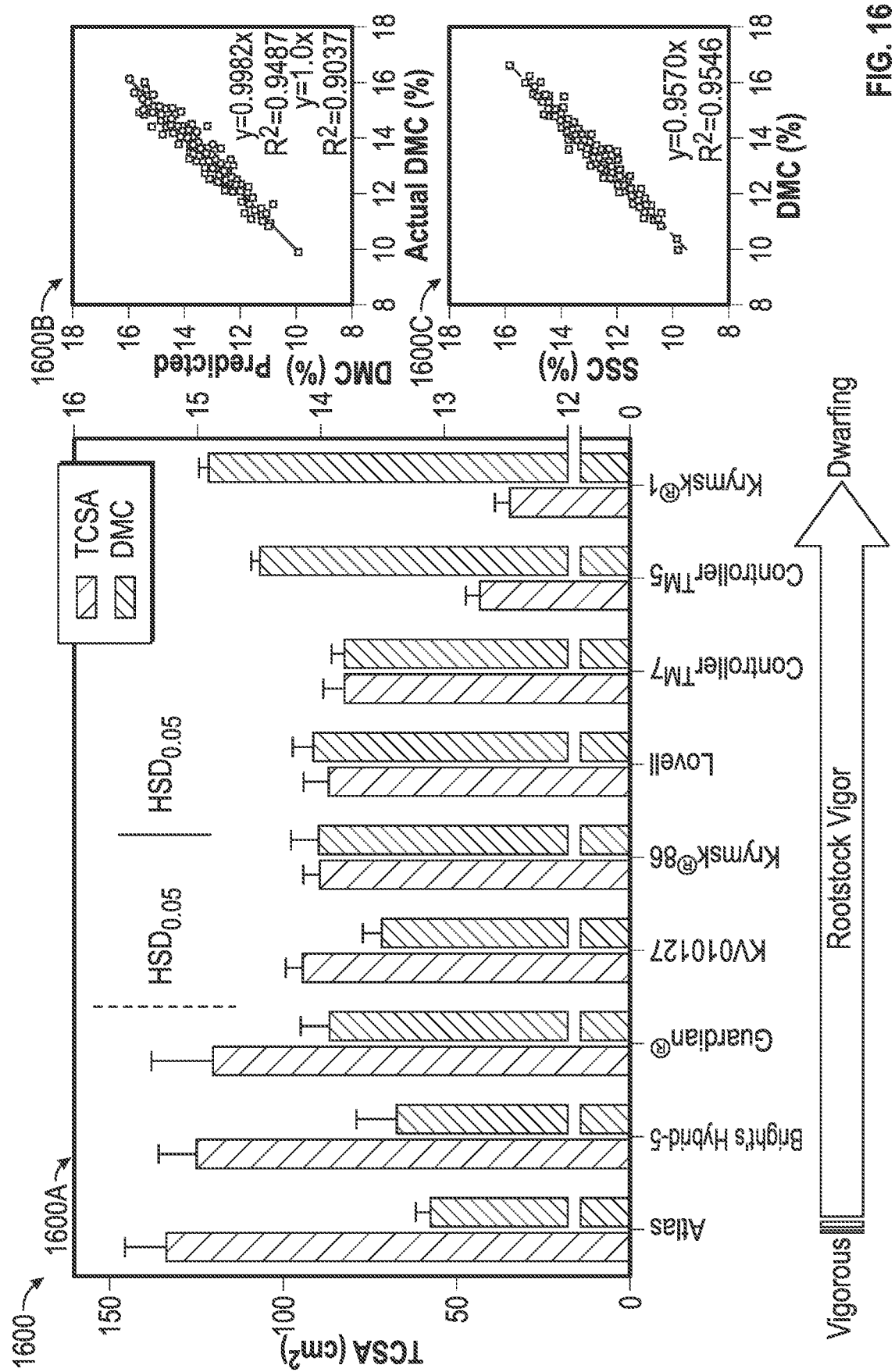
FIG. 16 exemplifies the effect of rootstock on peach productivity by comparing TCSA and dry matter content.

FIG. 16 exemplifies the effects 1600 of rootstock on peach productivity by showing an exemplary comparison 1600A of trunk cross-section area ("TCSA") and fruit dry matter content, graphed alongside a comparisons of predicted DMC and actual DMC (1600B) and actual SSC and DMC (1600C) in 'Redhaven' scions.

Working Example(s)

1.0 Experimental Approach for NIRS Prediction Models Calibration and Validation

Figure 17A:
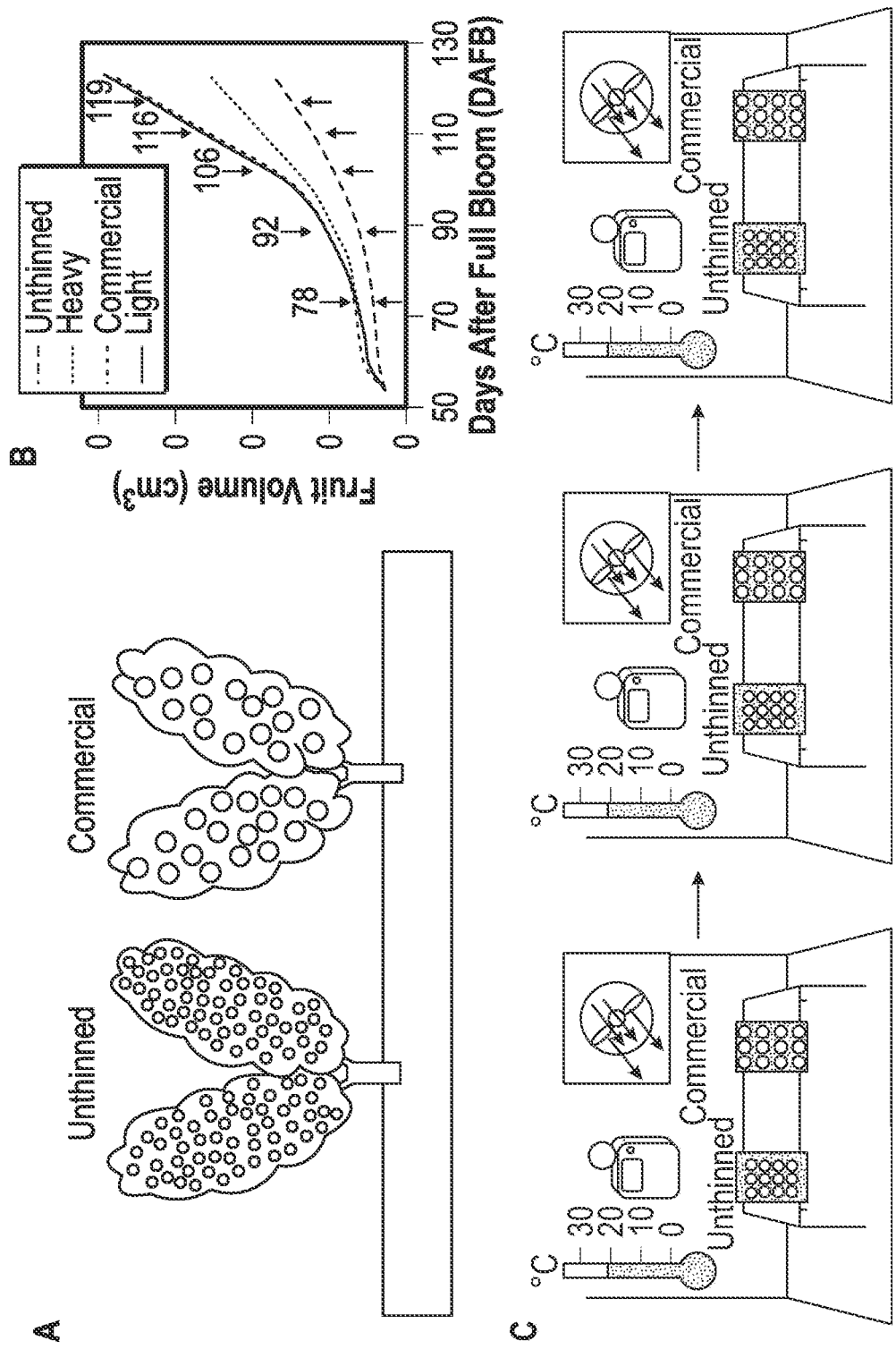
FIGS. 17A-C work an example of a Vis-NIRS-based non-destructive model development approach, with the results of using said model shown in FIGS. 17A-C relating to the 'Sierra Rich' cultivar.
Figure 17B:
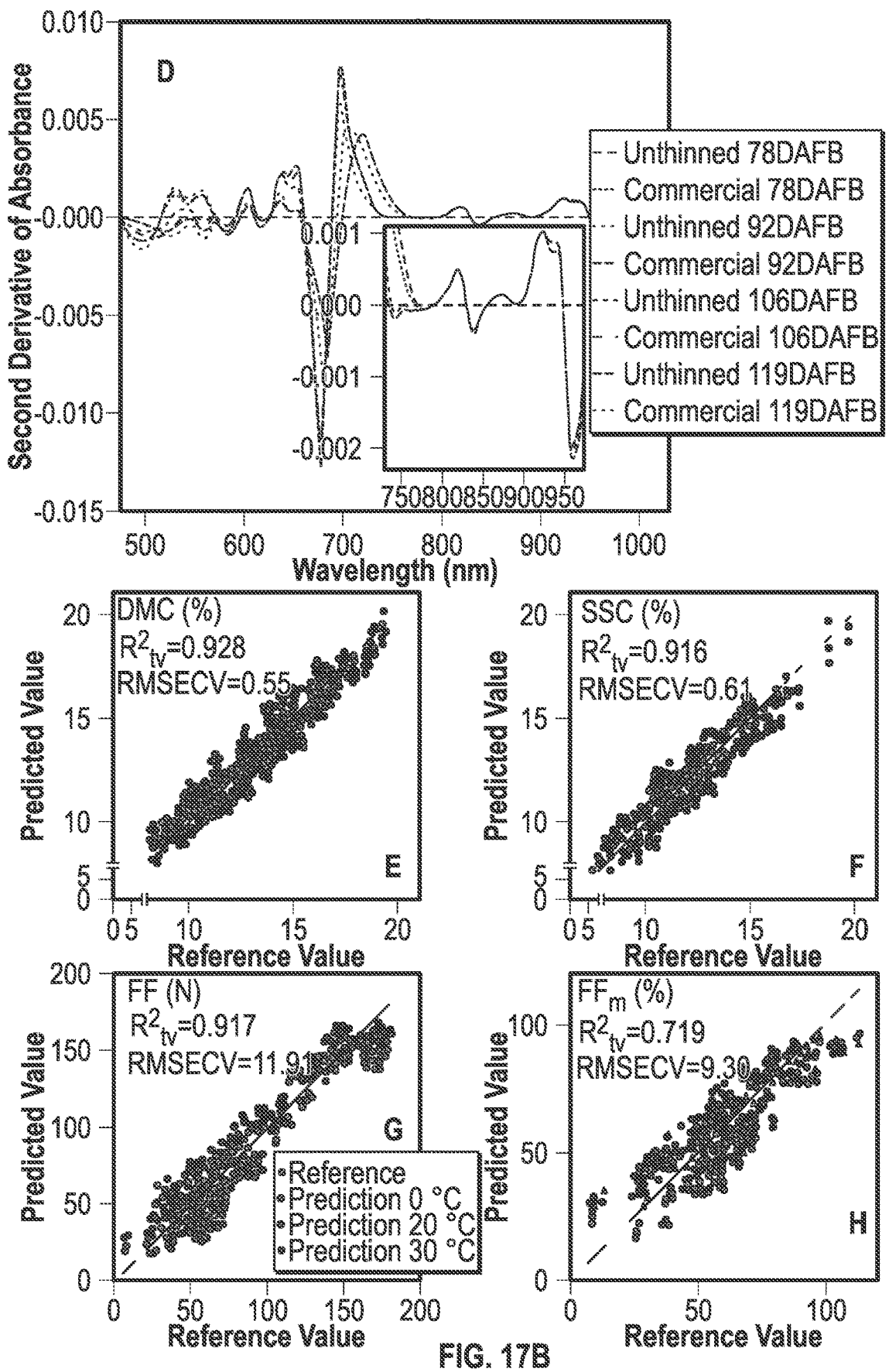
Figure 17C:
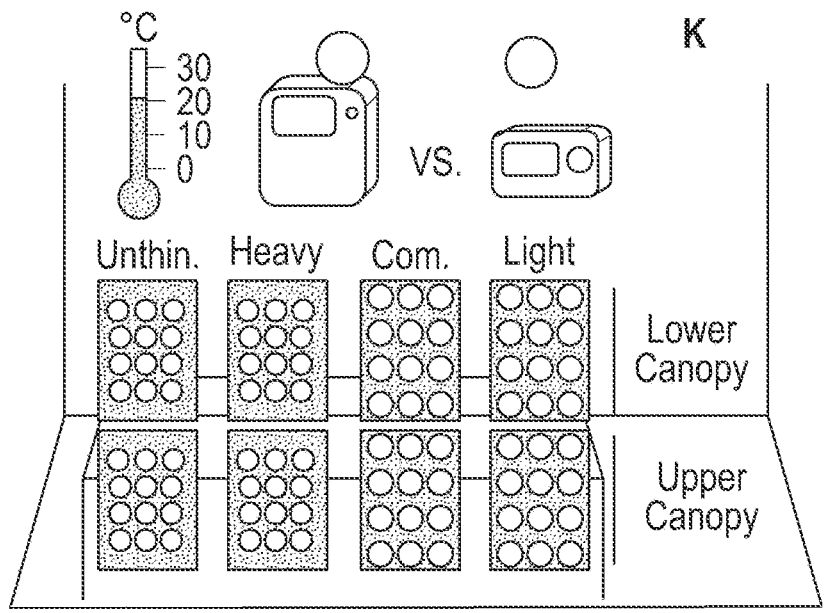
Figure 17C:
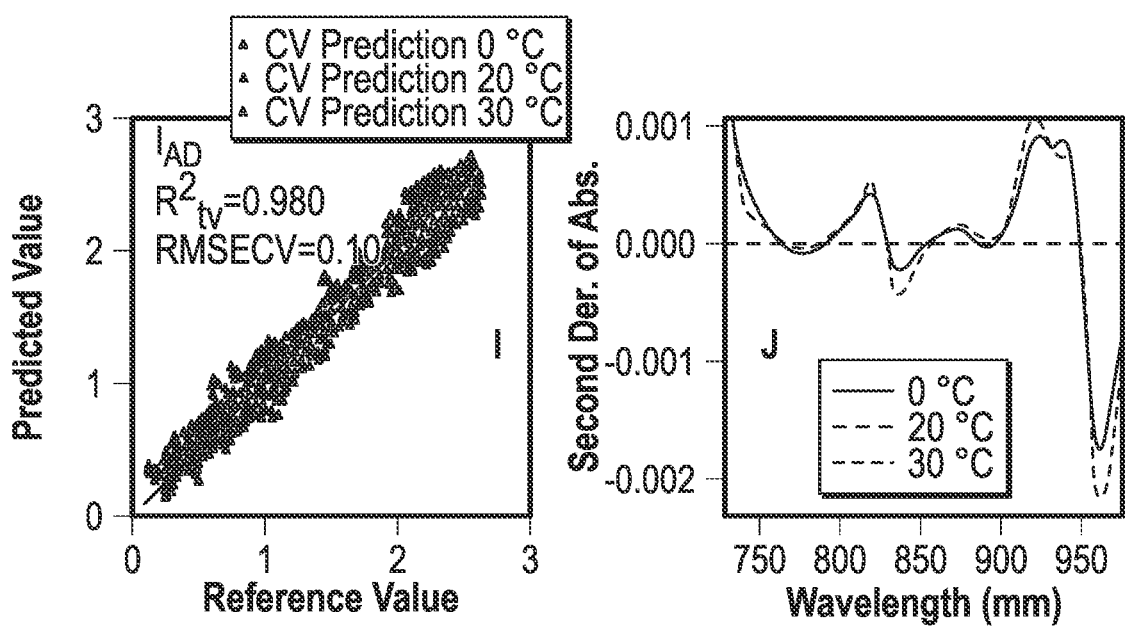

A crop load experiment was conducted to generate a broad range of internal fruit quality across distinct maturity levels for the development of a non-destructive peach quality and maturity model. Fruit coming from unthinned and commercially thinned trees were sampled at different developmental stages at 78, 92, 106, 116 and 119 days after full bloom (DAFB) (FIG. 17A, area A). The impact of crop load management on 'Sierra Rich' peach fruit (a fully red overcolored fruit) growth curve was assessed in unthinned and commercially thinned trees, as well as in two additional crop load levels (heavy and light). Arrows indicate sampling time in days after full bloom (DAFB) for multivariate non-destructive model calibration and the vertical bar represents the least significant difference based on Tukey's HSD test (P=0.05) (FIG. 17A, area B). Sampled calibration fruit were scanned with the handheld spectrometer at three temperatures (0, 20 and 30° C.) prior to reference value measurements to minimize the effect of the temperature on fruit tissue's second derivative spectral transmission (FIG. 17A, area C). Effect of crop load (unthinned and commercially thinned trees) on 'Sierra Rich' peach Vis-NIR spectra's second derivative of absorbance at different developmental stages (78, 92, 106 and 119 DAFB). 'Sierra Rich' peach NIR second derivative of absorbance at the spectral range 729-935 nm, that was used for dry matter content (DMC) and soluble solids concentration (SSC) calibration, are shown in the precluded plate. Arrows indicate the same regions of the spectra in both graphs (FIG. 17B, area D). Internal cross-validation of the predicted values at the different temperatures through the created regression models using the 'leave one out' method. Coefficient of determination of cross-validation ($R^2$) and root mean square error for cross-validation (RMSECV) for DMC (FIG. 17B, area E), SSC (FIG. 17B, area F), flesh firmness (FF, FIG. 17B, area G), FF for mature fruit (FFm, FIG. 17B, area H) and index of absorbance difference (IAD, FIG. 17C, area I) are shown in each particular figure plate. Influence of temperature (0, 20 and 30° C.) on peach fruit tissue's second derivative absorbance at DMC and SSC calibration spectral range (729-935 nm) (FIG. 17C, area J). Large-scale independent and field non-destructive model validation at harvest (123 DAFB) on fruit harvested from the different crop loads (unthinned, heavy, commercial and light) and canopy positions [lower (<1.4 m) and upper (>1.4 m) canopy] by comparing non-destructive predicted values with actual values from destructive assessment (FIG. 17C, area K).

To generate accurate non-destructive peach [*Prunus persica* (L.) Batsch] maturity and quality prediction models, a crop load×fruit developmental stage experimental calibration approach was followed. To implement this approach we used 26 'Sierra Rich' peach trees (using 'Lovell' as the rootstock) that were grown under standard conditions at the Colorado State University's experimental orchard at Western Colorado Research Center-Orchard Mesa, Grand Junction, CO. Experimental 9-year old peach trees, were planted at a planting density of 1436 trees per ha (planting distances: 1.5×4 m) and trained in a perpendicular-V system. Fifty-two days after full bloom (DAFB) ten trees were thinned to a commercial crop load level, ten were left unthinned, and the remaining six were thinned to a heavy or light crop load (three trees per treatment). To reach the desired crop load levels, thinning was applied in a way that one fruit every 5, 15 or 30 cm per shoot was left to form the heavy, commercial and light crop load levels, respectively.

Seventy fruits from seven unthinned and seven commercially thinned trees (35 fruit per thinning treatment, 5 from each tree) were sampled across five different developmental stages [stage 2 (S2, 78 DAFB), initiation of S3 (92 DAFB), S3 (106 DAFB), S4I (116 DAFB), S4II (119 DAFB)] and served as the calibration population (350 fruits total) for NIRS prediction models creation (FIG. 17A, areas A and B). At the commercial harvest stage (123 DAFB as defined for the commercial crop load treatment) a group of 150 fruits was harvested from the seven unthinned and commercially thinned trees to form the independent validation population (validation data). The three trees of the two additional crop load treatments, heavy and light, along with the remaining three trees from the unthinned and commercial crop loads were used for field validation only (field data). During commercial harvest, peach tree canopies across all crop load treatments were separated in two layers, below 1.4 m (lower canopy) and above 1.4 m (upper canopy). Fruit harvested from each layer were used to evaluate the effect of canopy position on peach fruit maturation and internal quality and to further validate the analytical capacity of the created non-destructive models (FIG. 17C, area K).

1.1 Peach Fruit NIR Spectral Acquisition

The calibration population was comprised of undamaged 'Sierra Rich' peaches, coming from unthinned and commercially thinned trees across five different developmental stages (S2, initiation of S3, S3, S4I, S4II) (FIG. 17A, areas A and B). Spectral measurements were taken using an 'open-type' handheld NIRS sensor (F-750 Produce Quality Meter, Felix Instruments Inc., Camas, WA, USA). In our approach the spectra of the second derivative of absorbance in the region of 310-1100 nm at 3 nm spectral sampling intervals were recorded across all fruit samples of the calibration population. Immediately after sampling at each developmental stage, each single fruit of the calibration population was numbered on both sides. This enabled two independent scans and reference values to be obtained per fruit for model development. To minimize the effect of temperature on model performance, due to associated changes in the molecular response to light absorbance of carbohydrates under different temperatures (FIG. 17C, area J), calibration fruit were exposed at three different temperatures: in a cold room (0° C., 95% RH) or in an incubator (20 and 30° C., 95% RH) (model I-36VL, Percival Scientific, Inc. Perry, Iowa, USA) prior to scanning. Fruit coming out of each temperature regime were then immediately scanned with the handheld spectrometer and then placed in the next temperature level (FIG. 17A, area C). Scanned fruit areas were precisely marked to make sure the NIRS scans across the different temperatures were taken at the exact same spot. After scanning across the different temperatures, reference values of internal quality and maturity were measured destructively and non-destructively in the numbered and marked areas of the calibration population fruit.

Dry matter content (DMC) was measured on one side of the fruit, while flesh firmness (FF) and soluble solids concentration (SSC) were measured on the other side. Reference values of the index of absorbance difference ($I_{AD}$), which was a non-destructive measurement were taken on both sides prior to any destructive measurements. Detailed information of reference value acquisition is provided in section 2.3 below.

1.2 Physiological Characterization and Reference Values Acquisition

Standard pomological parameters were used to fully characterize and justify the crop load×developmental stage and fruit canopy position experiments that were used for the calibration and validation of Vis-NIRS prediction models, respectively, as shown in Tables 1-2 below:

TABLE 1

Effect of crop load on 'Sierra Rich' peach yield, fruit size, internal quality and maturity at harvest with respect to various pomological parameters. 'Sierra Rich' peach trees were thinned at different levels (heavy, commercial and light) and compared to unthinned controls.

| | Pomological parameters | | |
|---|---|---|---|
| Crop load | Crop Load (Fruit no. tree$^{-1}$) | Crop load (fruit no. cm$^{-2}$ of TCSA) | Yield (kg · tree$^{-1}$) |
| Unthinned | 379.7 ± 8.8$^a$ | 4.5 ± 0.3$^a$ | 32.7 ± 3.1$^a$ |
| Heavy | 159.3 ± 19.1$^b$ | 2.0 ± 0.1$^b$ | 21.7 ± 2.9$^b$ |
| Commercial | 65.7 ± 4.8$^c$ | 0.8 ± 0.1$^c$ | 11.8 ± 0.9$^c$ |
| Light | 32.3 ± 6.4$^d$ | 0.4 ± 0.1$^d$ | 6.1 ± 1.2$^d$ |

| | Pomological parameters | | |
|---|---|---|---|
| Fruit FW (g) | Fruit size (diameter, mm) | TSCA increase (%) | Return bloom (flower no. m$^{-1}$) |
| 86.0 ± 6.9$^c$ | 54.9 ± 0.5$^c$ | 5.3 ± 0.6$^c$ | 14.4 ± 2.1$^b$ |
| 139.0 ± 8.0$^b$ | 60.2 ± 1.2$^b$ | 9.2 ± 1.5$^{bc}$ | 22.3 ± 3.7$^{ab}$ |
| 179.2 ± 2.5$^a$ | 65.9 ± 1.1$^a$ | 12.1 ± 1.4$^{ab}$ | 25.3 ± 3.7$^{ab}$ |
| 192.1 ± 10.0$^a$ | 68.5 ± 0.6$^a$ | 16.1 ± 1.5$^a$ | 30.7 ± 3.3$^a$ |

TABLE 2

Effect of crop load on 'Sierra Rich' peach yield, fruit size, internal quality and maturity at harvest with respect to various fruit quality and maturity parameters. 'Sierra Rich' peach trees were thinned at different levels (heavy, commercial and light) and compared to unthinned controls.

| | Fruit quality and maturity parameters | | |
|---|---|---|---|
| Crop load | DMC (%) | SSC (%) | TA (malic acid, %) |
| Unthinned | 10.9 ± 0.6$^b$ | 10.1 ± 0.4$^c$ | 0.8 ± 0.0$^{bc}$ |
| Heavy | 11.9 ± 0.4$^b$ | 11.3 ± 0.4$^b$ | 0.7 ± 0.0$^c$ |
| Commercial | 14.0 ± 0.4$^a$ | 13.3 ± 0.4$^a$ | 0.9 ± 0.1$^a$ |
| Light | 14.1 ± 0.3$^a$ | 13.4 ± 0.4$^a$ | 0.9 ± 0.0$^a$ |

| | Fruit quality and maturity parameters | | |
|---|---|---|---|
| FF (N) | $I_{AD}$ | Lightness (L*) | Hue angle (h°) |
| 46.6 ± 4.8$^a$ | 1.0 ± 0.1$^a$ | 40.4 ± 0.6$^a$ | 34.1 ± 0.8$^a$ |
| 34.3 ± 4.4$^{ab}$ | 0.7 ± 0.1$^b$ | 39.3 ± 0.6$^a$ | 32.4 ± 0.9$^{ab}$ |
| 37.1 ± 5.7$^{ab}$ | 0.6 ± 4.8$^{bc}$ | 38.9 ± 0.5$^a$ | 31.1 ± 0.6$^{bc}$ |
| 24.2 ± 4.9$^b$ | 0.4 ± 4.8$^c$ | 36.9 ± 0.6$^b$ | 29.4 ± 0.6$^c$ |

Trunk cross sectional area (TSCA, cm$^{-2}$) was calculated via circumferential measurements prior to thinning and after leaf drop, to evaluate tree growth as a response to crop load management. Fruit growth (diameter, mm) was measured in 10 fruit per tree on the three replicated validation trees across all crop load treatments. Measurements took place the day prior to thinning, immediately after thinning and every week throughout the rest of the growing season until harvest (FIG. 17A, area B). Harvest parameters that were measured across crop loads and canopy positions included: crop load (expressed as fruit number per cm$^2$ of TSCA or fruit number per tree), yield (kg·tree$^{-1}$), fruit fresh weight (FW, g) and fruit size (diameter, mm). To characterize the effect of crop load on floral bud initiation and return bloom in March 22$^{nd}$ of the following year, the total number of flowers on five shoots per tree were counted at 50% full bloom. Additionally, the length of each shoot was measured to calculate the blossom density (expressed as flower number per m of shoot length).

Fruit internal quality in terms of DMC was estimated by the difference in mass between the fresh sample of peach mesocarp tissue and the equivalent dry sample. Collectively, peach mesocarp was removed from the side of the fruit using a 25-mm diameter cork borer and immediately weighed to the nearest 0.001 g with a digital scale (TC-204, Denver Instrument Company, Arvada, CO). The samples were then dried in an oven (VWR® Forced Air Oven-104 L, VWR, Radnor, PA) at 65° C. for 72 h as previously described. The results were expressed as DMC percentage (%) by dividing the dried mass with the fresh mass and multiplying by 100. Soluble solids concentration was determined with a digital refractometer, model PR-32α (Atago, Tokyo, Japan) with automatic temperature compensation. Measurements were performed on juice drops coming from peach mesocarp samples that were previously removed with the 25-mm cork borer and squeezed within a garlic press. Titratable acidity (TA) was determined in 5 mL of juice coming from bulked mesocarp tissue from 5-fruit replicates diluted in 50 mL of DI water. Titration was accomplished with 0.1 mol·L$^{-1}$ NaOH as the titrant that was poured through a digital burette (model Top Buret™ M-25 mL, Eppendorf, Hauppauge, NY) to an inflection point of pH 8.2 that was determined with a pH meter (model SevenCompact S220, Mettler Toledo, Columbus, OH). Results were finally expressed as percentage of malic acid (%).

Fruit maturity was assessed with two parameters: the flesh firmness (destructive) and the index of absorbance difference ($I_{AD}$, non-destructive). Flesh firmness (FF) was determined with a digital fruit texture analyzer (model FR-5120, Lutron Electronic Enterprise Co., Taipei, Taiwan) equipped with an 8-mm diameter stainless probe. Analysis was accomplished on a single side per fruit that was previously peeled with 1-mm thick skin tissue removed. Individual fruit were analyzed on opposite sides at the equatorial region.

Results that corresponded to the maximum force applied by the probe to penetrate into the fruit flesh by 10 mm expressed in newtons (N). Index of absorbance difference ($I_{AD}$) measurements were taken non-destructively with a handheld factory calibrated (closed type) Vis-NIRS sensor (DA-meter®, T. R. Turoni srl, Forli, Italy).

Fruit skin color was measured with a portable colorimeter that was calibrated using the manufacturer's standard white plate (Minolta CR-20, Minolta, Osaka, Japan). Two measurements at two opposite equatorial sides of the fruit were carried out. Skin color changes were expressed using lightness (L*) and hue angle (h°) values.

Statistical differences among crop load treatments, developmental stages and canopy positions were calculated using ANOVA at P=0.05 in statistics package SPSS 25.0 for Mac OS X (SPSS, Chicago, IL, USA). Graphs were created using Prism v8.3 for Mac OS X (Graph Pad Inc., San Diego, CA, USA).

1.3 Development of Multivariate Prediction Models

'Sierra Rich' fruit spectral measurements at the three different temperatures (0, 20 and 30° C.) and the corresponding reference values were entered into the manufacturer's 'Model Builder' software (F-750 Produce Quality Meter, Felix Instruments Inc., Camas, WA, USA). Second derivative absorbance spectra of specified ranges from the calibration scans correlated with reference values of internal quality or maturity. A regression coefficient was then calculated with a non-linear iterative partial least squares (NI-PALS) regression. Finally, a regression model was created, which could be loaded onto the handheld device and be used to non-destructively predict the values of the modeled parameters of internal quality and/or maturity. Spectral ranges for model creation were selected based on preliminary studies, literature searches and manufacturer's instructions. More specifically, 729-935 nm were used for DMC and SSC, 477-657 nm were used for FF and 600-750 nm were used for IAD (FIG. 17B, area D). During each scan measurement, the regression model processed the second derivative of absorbance of the defined range of spectra by multiplying each wavelength's absorbance by the regression coefficient and all outcomes were summed. The predicted value was finally calculated by adding the intercept coefficient of the model (Felix Instruments Inc., Camas, WA, USA). The handheld device has the capacity to record up to three modeled parameters at the same time with a single scan, however, only two are displayed on the screen.

1.4 Prediction Model Statistics and Validation in the Lab and the Field

The leave-one-out cross-validation (LOOCV) statistical analysis through an internal cross-validation theoretically estimated the predictability of each specimen that constitutes the created regression models by excluding it from the analysis of the calibration data set for each regression model. Root mean square error for cross-validation (RMSECV), coefficient of determination of cross-validation ($R^2$cv) and predicted residual error sum of squares cross-validation (PRESSCV) were obtained following comparisons between predicted versus reference values of the calibration population. These parameters provided a summary measure of the fit of the regression models to a sample of observations that included the calibration population (FIG. 17B, area E and Tables 3-4, shown below).

TABLE 3 calibration information of the created non-destructive prediction models of peach internal quality and maturity

| | Calibration | | | | | | |
|---|---|---|---|---|---|---|---|
| Parameter | Spectral range (nm) | N | Reference values range | Factor (PC) | $R_{CV}^2$ | RMSECV | PRESS |
| DMC (%) | 729-975 | 346 | 7.8-20.9 | 9 | 0.928 | 0.55 | 0.30 |
| SSC (%) | 729-975 | 325 | 6.9-19.7 | 10 | 0.916 | 0.61 | 0.38 |
| FF (N) | 477-657 | 293 | 7.3-213.9 | 10 | 0.917 | 11.91 | 142.01 |
| $FF_m$ (N) | 477-657 | 205 | 7.1-123.0 | 10 | 0.719 | 9.30 | 82.53 |
| $I_{AD}$ | 600-750 | 695 | 0.0-2.6 | 8 | 0.980 | 0.10 | 0.01 |

TABLE 4 regression statistics of the independent validation of the created non-destructive prediction models of peach internal quality and maturity

| | Validation | | | | | | |
|---|---|---|---|---|---|---|---|
| Parameter | Spectral range (nm) | N | Reference values range | $R_{CV}^2$ | RMSEP | RMSEP % | Bias |
| DMC (%) | 729-975 | 150 | 7.4-20.2 | 0.983 | 0.41 | 2.92 | 0.25 |
| SSC (%) | 729-975 | 150 | 6.5-18.3 | 0.958 | 0.58 | 4.39 | −0.14 |
| FF (N) | 477-657 | 150 | 3.6-83.3 | 0.426 | 13.04 | 26.29 | 6.58 |
| $FF_m$ (N) | 477-657 | 100 | 5.2-74.6 | 0.610 | 9.87 | 21.55 | 2.71 |
| $I_{AD}$ | 600-750 | 300 | 0-1.7 | 0.961 | 0.08 | 11.56 | 0.02 |

Root mean square error for cross-validation was plotted against PCs to define optimum PC number for each regression model. To identify outliers within the calibration population, the leverage criterion and the studentized residuals were used. The leverage criterion represents the influence of each sample in the regression model. The studentized residual analysis was effective in detecting outliers and assessing the equal variance assumption. A studentized residual that fell outside of the normal distribution's limits of variance, with a confidence level of 95%, was considered as a potential outlier.

Finally, regression data of an independent validation at commercial harvest stage (123 DAFB, see section 2.1), using a separate fruit population (n=150), were tested for linearity ($R^2$) and RMSEP to determine the accuracy of the created models in predicting DMC, SSC, FF, and $I_{AD}$ (validation data). The scanned areas of these fruits were carefully marked to record reference values in a similar way to the calibration set assuring that all of the comparisons of predicted and actual values were coming from the same spots of the fruit. The predictive performance of the developed models was tested through correlation coefficient of validation ($R^2$) along with RMSEP. Model accuracy was further characterized with RMSEP % corresponding to the percentage of prediction error that was calculated with RMSEP that was divided by the mean values of fruit quality/maturity parameters from the independent group of validation. Bias that corresponds to the difference between mean predicted and mean actual values was also used for model accuracy characterization (Tables 3-4). Reference and corresponding predicted values were plotted across all modeled maturity and quality parameters to provide a better visualization of the results (FIGS. 17B-C and 18A-B).

An extra step on the model creation was taken to assure that the analytical capacity of NIRS to predict FF was fairly judged. Because the original calibration population comprised fruit ranging from very immature and firm (FF=213.9 N) to commercially mature and ripe (FF=7.3 N) with a significant portion of fruit having FF>100 N (FIG. 17B, area G and Tables 3-4), a new FF model could be created following a post-processing approach to more accurately predict FF on mature fruit (FFm) close to harvest. A similar post-processing approach with the same calibration populations for DMC, SSC and $I_{AD}$ did not provide any improvements on the predictive performance of their models (data not shown).

Since the model calibration population included fruits coming from different developmental stages, the accuracy of the developed models was assessed on fruits that were independently harvested (76, 96 and 113 DAFB) from the calibration population and scanned with the handheld device to obtain the second derivative spectra. The same fruits were also assessed for reference values at the marked areas that were used for NIR scans. Since the regression models were developed later in the same growing season, a model post-processing approach was followed as described above. Second derivative spectral data for the wavelengths of interest from the scanned fruit and the regression coefficients of the developed regression models for DMC, SSC, FF, and $I_{AD}$ were multiplied to calculate the predicted values. Finally, these post-processing predicted values were compared with the reference values for linearity ($R^2$) and RMSEP to characterize predictive performance of the regression models during fruit growth and development.

The developed regression models were further used in the field to fully characterize the effect of crop load and canopy position on peach fruit maturity and internal quality. During commercial harvest (123 DAFB, see section 2.1), three tree canopies across all crop load treatments (unthinned, heavy, commercial and light crop load) were separated in two layers, below 1.4 m (lower canopy) and above 1.4 m (upper canopy). Ten harvested fruit (20 scans) from each layer and tree (60 scans per treatment) were used to evaluate the effect of fruit canopy position on peach maturation and internal quality. Data coming from this intermitted experiment were used to further validate the analytical capacity of the created non-destructive models (FIG. 17C, area K). Reference quality and maturity was assessed on the two equatorial sides of the fruit (field data), rather than on precisely marked areas, as during independent model validation.

Principal component analyses (PCA) on predicted data and second derivative of absorbance spectral data (400-1100 nm) from fruit coming from distinct canopy positions across crop loads was performed using JMP® Pro v13.2 (SAS Institute Inc., Cary, NC, USA). Calibration cross validation and regression data from the independent and field validations of the developed peach quality and maturity models, as well as graphs were generated using Prism v8.3 for Mac OS X (Graph Pad Inc., San Diego, CA, USA).

2.1. Effect of Crop Load on Peach Fruit Quality and Maturity

Among the different preharvest and orchard factors that can influence peach fruit internal quality crop load management is the most impactful. Based on this fact, an experiment that could reproduce a broad range of fruit internal qualities, sufficient for robust non-destructive models development, was designed. In this experiment 'Sierra Rich' trees were left unthinned or thinned to a heavy, commercial or light crop load level. Crop load significantly affected peach fruit volume during growth and development (FIG. 17A, area B) as well as yield, quality and maturity parameters at harvest and more interestingly, return bloom the next season (Tables 1-2). More specifically fruit thinning to a heavy crop load (one fruit left every 5 cm) had a significant impact on fruit yield reduction by 56% when expressed as fruit count per $cm^2$ of TCSA, and by 34% in kg of fruit per tree at harvest compared to the unthinned trees. Similarly, the heavy crop load significantly increased average fruit fresh weight by 62% and average fruit size by 10% (diameter, mm) when compared to the unthinned trees. On the other hand, increased thinning to a commercial crop load level (one fruit left every 15 cm) resulted in 82% less fruit per $cm^2$ of TCSA, and 64% less kg of fruit per tree at harvest compared to the unthinned trees. This thinning strategy doubled average fruit fresh weight in grams and increased average fruit size by 20% compared to the unthinned trees. It is worth mentioning that, increased thinning severity to extreme levels (light crop load, one fruit left every 30 cm) further reduced fruit count by 51% when calculated per $cm^2$ of TCSA, as well as yield by 48% (in kg per tree) when compared to the commercial crop load without a significant increase in average fruit weight and size at harvest (Tables 1-2).

Crop load management significantly affected fruit internal quality and maturity as it was destructively and non-destructively determined at harvest. Fruit thinning and lighter crop loads increased fruit internal quality parameters as defined by DMC, SSC and TA (Tables 1-2). More specifically, the commercial crop load gave fruit with approximately 3% more DMC and SSC compared to unthinned trees, while the light crop load did not improve these parameters any further from the commercial crop load. Interestingly, heavy crop load increased SSC levels by approximately 1% compared to unthinned trees (Tables 1-2). It is broadly accepted and scientifically proven that consumers can detect differences in SSC at 1% among fruit samples. Thus, the results of the impact of crop load management on fruit internal quality underscore the importance of thinning to improve consumer acceptance. Titratable acidity (TA) was increased in fruit coming from commercially thinned trees and the same trend was found with the light crop load trees. The TA difference between heavy and unthinned trees might be associated with differences in maturity status (Tables 1-2).

The excess reduction in total number of fruits by extreme thinning resulted in a significant increase in tree size as expressed with the percentage increase of TCSA at the end of the growing season (Tables 1-2). This effect of the light crop load promoting tree vigor and vegetative growth might have compromised the impact of this extreme thinning strategy on fruit size and quality. Conditions promoting tree vigor can increase competition between growing fruit and growing vegetative parts for photosynthesis products, as well as reduce sunlight within the fruit producing parts of the canopy. This further highlights the need for optimized crop load management for acceptable yields and balanced vegetative growth for optimal light distribution and maximum fruit quality.

Crop load management was also associated with differences in peach fruit maturity (Tables 1-2). Lighter crop loads promoted maturation as was measured using destructive (FF) and non-destructive ($I_{AD}$) methodology. Based on the results of our study and on commercial and light crop load fruit characteristics at harvest, an $I_{AD}$=0.6 would be an optimum index of commercial maturity (well-mature FF~40 N) for 'Sierra Rich' and $I_{AD}$=0.4 for 'tree ripe' maturity (FF~30 N). The same effect of crop load on fruit maturity was captured with skin color measurements, with decreased lightness (L*) and hue angle (h°) that represent a deeper red color in the skin. This deeper red overcolor was observed on the fruit coming from the lighter crop loads, when compared to fruit coming from unthinned trees (Tables 1-2).

Figure 18A:
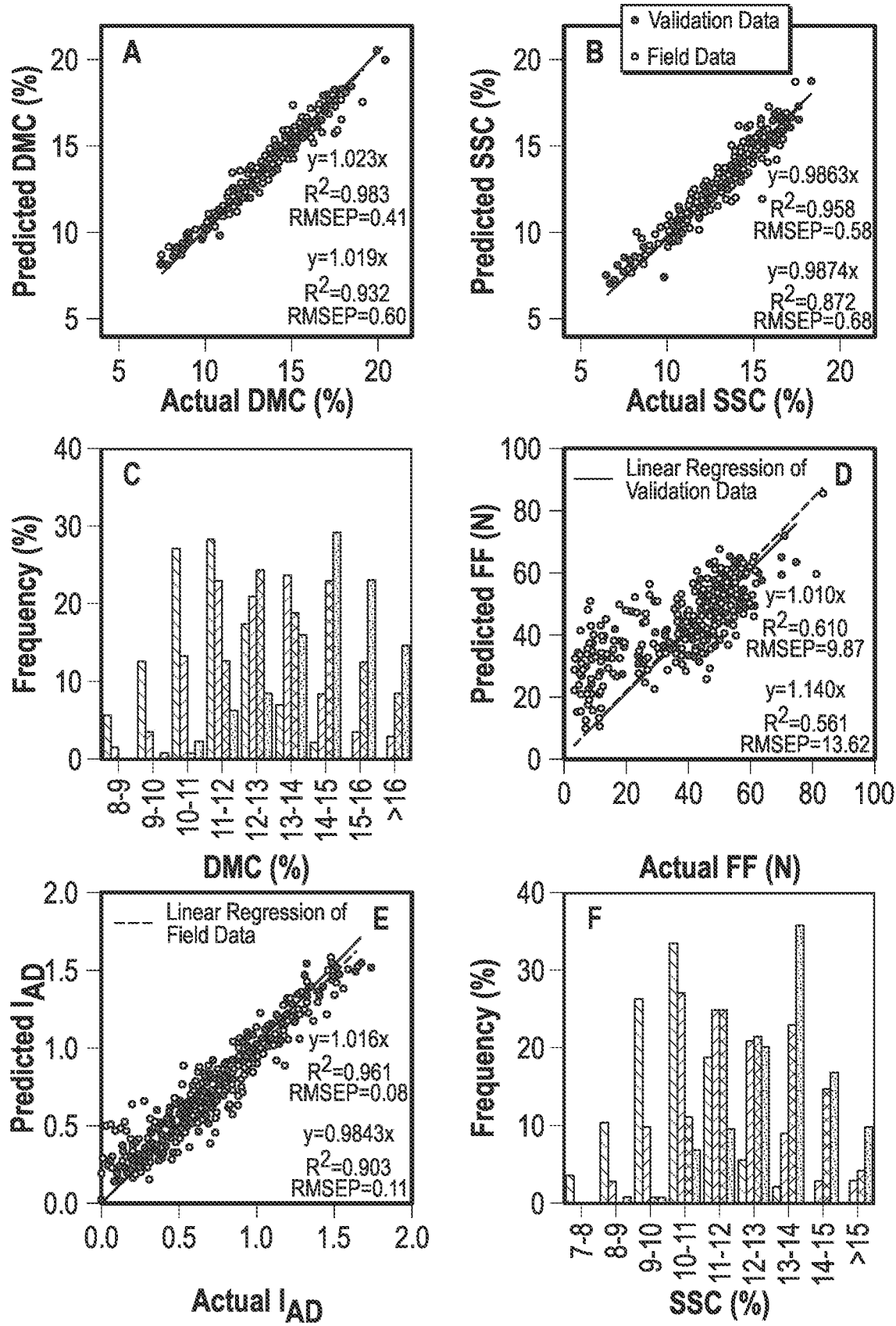
FIGS. 18A-B validate a non-destructive Vis-NIRS regression independent model to by comparing predicted values from the model in the lab with data taken in the field at harvest for the 'Sierra Rich' cultivar.
Figure 18B:
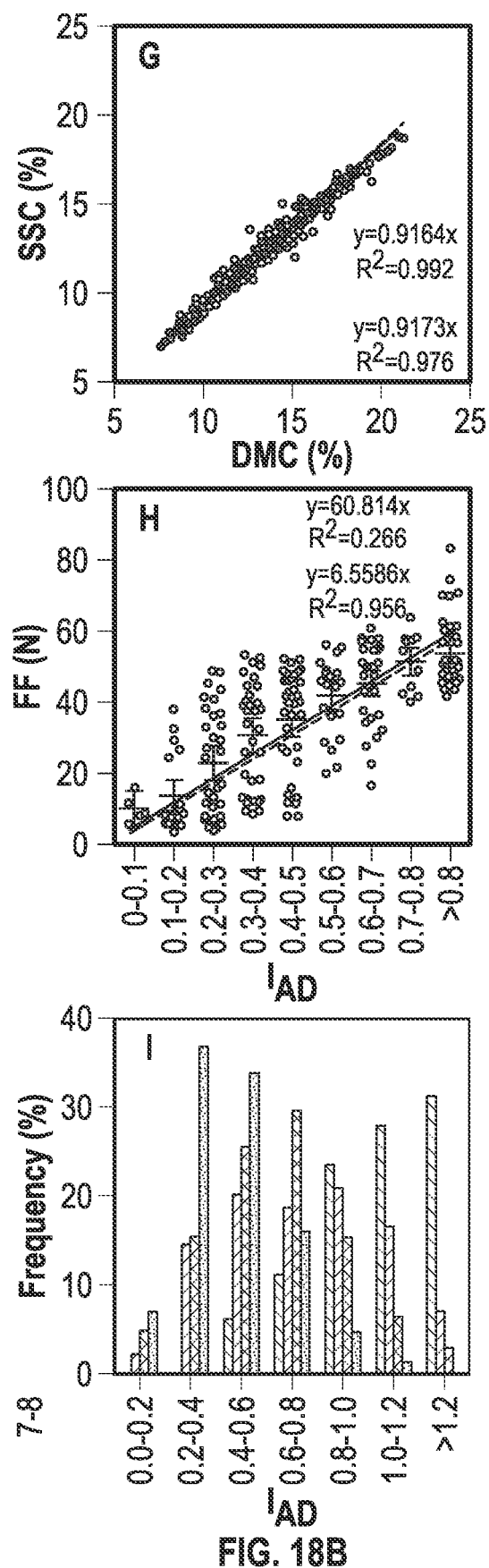

2.2. Fruit Internal Quality and Maturity can be Accurately Predicted Non-Destructively with NIR The novel experimental approach of crop load management×fruit developmental stage provided a broad range of peach internal qualities at similar maturity levels during fruit growth, development and at harvest. This was an ideal biological system for the calibration of non-destructive models to predict peach quality and/or maturity prior to the commercial harvest stage, as well as at harvest. Reference value ranges for the calibration population were 7.8-20.9% for DMC, 6.9-19.7% for SSC, 7.3-213.9 N for FF and 0-2.6 for $I_{AD}$ (Tables 3-4), further highlighting the impact of the crop load×fruit developmental stage approach on the creation of these varying levels of peach internal quality and maturity. This variable fruit material was utilized for a large-scale Vis-NIR spectra acquisition to develop precise and reliable multivariate regression models for non-destructive peach fruit physicochemical and maturity assessments. Non-destructive regression models for predicting DMC and SSC, as well as $I_{AD}$ and FF, in 'Sierra Rich' peaches, were developed using fruit samples coming from different crop loads (unthinned and commercially thinned trees) and developmental stages (S2, S3, S4I, S4II) (FIG. 17A, areas A-B). Selected fruits across a range of internal quality at different maturity levels and sizes were scanned using a non-destructive 'open type' hand-held NIRS sensor at three different temperatures (0, 20 and 30° C.) to obtain temperature-compensated models and to minimize the impact of temperature on the second derivative absorbance spectra (FIG. 17C, area J). By scanning at different temperatures (FIG. 17A, area C), the created models were able to ignore any spectral shifts or changes that are irrelevant to the traits of interest (FIG. 17C, area J). Such approach will potentially accommodate any need for use under varying temperature conditions such as the field, lab, retail store, cold storage room, packinghouse or grocery store which represents the significant realms of the fresh produce supply chain. Regression data were tested for linearity ($R^2$), RMSECV and PRESSCV to determine the potential for reliable quality and maturity estimates from the created models (Tables 3-4, FIGS. 17B-C, areas E-I). This performance evaluation approach of the created regression models gave a high $R^2$ and relatively low RMSECV and PRESS values across most of the created models (Tables 3-4, FIGS. 17B-C, E, F & I), with FF being the exception from this rule (Tables 3-4, FIG. 17B, areas G-H). These results indicated a strong potential for a successful regression model development across both internal quality (DMC, SSC) and maturity (only $I_{AD}$) parameters, with a questionable outcome for FF. However, this was only a theoretical estimation of the predictive accuracy of the created models. To confirm whether or not the created models were able to perform reliable predictions in fruit internal quality and maturity, a second population of fruit (n=150) were used to independently validate the models (Tables 3-4 and FIGS. 18A-B). During harvest, at the commercial maturity stage (123 DAFB) 150 fruits were harvested from unthinned and commercially thinned trees. These fruits were scanned with the handheld Vis-NIRS sensor that was operating with the developed models, and reference values were measured soon after on the marked areas where Vis-NIRS scans were taken. Regression statistics of the independent validation of the created models showed that internal quality models (DMC, SSC) can accurately be predicted with NIRS. More specifically, independent validation of the DMC regression model gave a $R^2=0.98$, RMSEP=0.41% and RMSEP %=2.92 with Bias=0.247 (Tables 3-4 and FIG. 18A, area A). Similarly, the independent validation of the SSC regression model gave a $R^2=0.96$, RMSEP=0.58%, RMSEP %=4.58 and Bias=−0.144 (Table 3-4 and FIG. 18A, area B). Non-structural carbohydrates (starch and sugars) can be affected by pre-harvest factors and their concentrations may vary across the different phases of fruit growth and development. It is noteworthy that high correlation was observed between DMC and SSC($R^2=0.99$) in the peach cultivar tested (FIG. 18B, area G). This could be due to the absence of starch in peach mesocarp, thus, DMC in peach can provide an accurate estimate of soluble sugars that are mainly represented with SSC. In most NIRS applications on non-destructive assessment of SSC and DMC in intact fruit that have been reported, a RMSEP of <1.0% hasn't been achieved so far when an independent population of fruit was used for validation. To our knowledge, this is the first report of such high accuracy in the prediction of these internal quality parameters with the application of a non-destructive approach in any fruit species that Vis-NIRS or other technologies have been utilized. This underscores the importance of the tree fruit physiology systems approach that was followed for non-destructive model calibration and validation.

In respect to the maturity parameters ($I_{AD}$ and FF), independent validations of the predictive performance gave two opposite outcomes. Prediction of the FF of mature peaches at harvest (independent validation population) was insufficient by the created regression model ($R^2=0.43$, RMSEP=13.04 N, RMSEP %=26.29, Bias=6.58) using the whole calibration population (Tables 3-4). For this reason, a post-processing model development approach was followed to test different scenarios of model calibration (see section 2.5). The best performance results came from the mature FF model (FFm) a model that was calibrated with the exclusion of 78 and 92 DAFB data. Although, FFm prediction performance ($R^2_v=0.61$, RMSEP=9.87 N, RMSEP %=21.55, Bias=2.71) was significantly improved (Tables 3-4 and FIG. 18A, area D) when compared to the original FF model, it was still considered insufficient. This suggests that the potential influence of secondary correlations is due to fruit characteristics that are not directly related to flesh firmness. Further work using different wavelength ranges, technologies (eg. hyperspectral imaging) and/or approaches (eg. focusing on specific maturity classes) are required to develop accurate non-destructive FF prediction models.

Contrary to the FF regression model performance, $I_{AD}$ can accurately be predicted with the 'open-type' handheld NIRS sensor (F-750 Fresh Produce Meter) used in our study. Independent validation showed a relatively high accuracy for predicting $I_{AD}$ in the spectral range of 600-750 nm ($R^2_v=0.96$, RMSEP=0.08, RMSEP %=11.56, Bias=0.024, Tables 3-4 and FIG. 18A, area E). Such a performance following our approach, indicates that an even more accurate prediction of $I_{AD}$ can be achieved with the same calibration population by fine-tuning the spectral ranges. $I_{AD}$ captures physiological changes (e.g., chlorophyll degradation) occurring during fruit maturation and ripening. When individual reference $I_{AD}$ values from the independent validation population were plotted against FF, it did not result in a correlation (FIG. 18B, area H). Although, a strong correlation of $I_{AD}$ with FF ($R^2=0.96$) was possible only when clustered $I_{AD}$ values were plotted against FF (FIG. 18B, area H). There were no correlations of $I_{AD}$ with any of the other parameters tested (data not shown). These findings are in agreement with previous reports that mentioned that this index does not correlate directly with traditional parameters used to identify maturity/quality status, such as FF or SSC, which makes it challenging for broad adaptation by producers. Based on the used handheld spectrometer specifications to record three measurements simultaneously, we tested the potential to predict fruit internal quality and maturity in the same spot on the fruit surface with a single scan. It is worth mentioning that this is the first report with extremely high accuracy on the determination of both internal fruit quality (DMC, SSC) and maturity ($I_{AD}$) with just a single scan. The use of this novel instrumentation setup will allow all fruit measurements to be segregated by maturity class, which is a highly regulated genetic parameter that heavily affects internal quality. Thus, the true impact of preharvest factors that affect fruit maturation, and subsequently internal quality, such as crop load, canopy position, rootstock, nutrition, etc. can now accurately and efficiently be determined.

2.3. Non-Destructive Assessment of the Impact of Peach Pre-Harvest Factors on Fruit Quality and Maturity in the Field These created multivariate non-destructive prediction models for fruit quality (DMC, SSC) and maturity (FF and $I_{AD}$) were further used for a large-scale study under actual field conditions to test the effect of preharvest factors on peach quality and maturity during growth, development and at harvest. A large number of fruits per treatment (n=150 per treatment or n=600 across all treatments) was used to non-destructively and destructively assess the effect of crop load on peach quality and maturity at harvest. Through this approach that served as a 'field validation', predicted values compared to actual reference values that were coming from the same side of fruit (but not precisely marked) (represented in "red" in FIG. 18A, A-B & D-E). Model prediction performance under field conditions was high for DMC, SSC and $I_{AD}$ with strong linearity ($R^2$) and low RMSEP. These results highlight the quality and accuracy of the regression models developed in the current study. On the other hand, performance of FF prediction models (FFm and FF, FIG. 18A, area D) appeared insufficient for field assessment.

The effect of preharvest factors on fruit internal quality cannot be completely captured with just an average value coming from a small sample of fruit, as traditional methodology dictates. Non-destructive technology developed and validated as accurate and reliable herein (DMC, SSC and $I_{AD}$), with its ability to quickly scan a large volume of fruit while still on the tree, can help fully characterize the influence of a given preharvest factor on fruit internal quality and maturity at very high resolution and precision. Thus, grower decisions can be supported by real-time large-scale data sets. These data sets can then be analyzed in a way that better aids in the understanding of a particular production management system (e.g., crop load), while at the same time it can be very informative from a commercial and financial standpoint.

Results showed that heavier crop loads reduced the percentage of fruit with high DMC and SSC (FIG. 18A, areas C & F) and increased the ones with low DMC and SSC. It has been demonstrated that a minimum of 11% SSC is required for most of mid-season peach cultivars to satisfy 80% of consumer acceptance. Based on this report's findings, unthinned trees had only 26% of their fruit satisfying this SSC threshold, whereas heavily cropped trees had 60%. On the other hand, trees that were thinned to commercial and light levels of crop load had 88 and 92% of their fruit exceed 11% SSC, respectively.

Heavier crop loads delayed fruit maturation (increased $I_{AD}$ values), while lighter loads advanced it. Minimum maturity levels for 'Sierra Rich' at commercial harvest in our study was established at $I_{AD}$=0.6 (well-mature FF~40 N). Only 6% of the fruit coming from unthinned trees were <0.6 at the day of harvest, whereas this percentage was 37, 46 and 78% for heavy, commercial and light crop loads, respectively (FIG. 18B, area I). This further demonstrates the importance of accurate, non-destructive and large-scale data acquisition to better characterize the effect of various preharvest factors on fruit maturity for optimum postharvest handling to maximize orchard quality outcome.

Our model development approach with the calibration fruit coming from different developmental stages across distinct crop loads allowed for strong model development with the potential for internal quality and maturity estimations during peach fruit growth and development. To evaluate predictive performance of the created models during fruit growth and development, an independent set of fruit coming from the different crop load treatments were sampled at different developmental stages (76, 96 and 113 DAFB) as well as at harvest (123 DAFB). These fruit samples were scanned with the handheld Vis-NIRS sensor and assessed for reference values. Predicted values for DMC, SSC and $I_{AD}$ were calculated through a post-processing model approach (see section 2.5). Two of the developed models FF and FFm were specifically used to predict FF of immature (76 and 96 DAFB) and mature (113 and 123 DAFB) fruit across the different developmental stages, respectively. Finally, these post-processing predicted values were compared with the reference values for linearity ($R^2$) and RMSEP. Results showed high predictivity and accuracy for DMC($R^2$=0.96 and RMSEP=0.55), SSC($R^2$=0.93 and RMSEP=0.64) and $I_{AD}$ ($R^2$=0.97 and RMSEP=0.09), and low for FF ($R^2$=0.82 and RMSEP=22.90) during fruit growth and development (FIG. 19).

Figure 19:
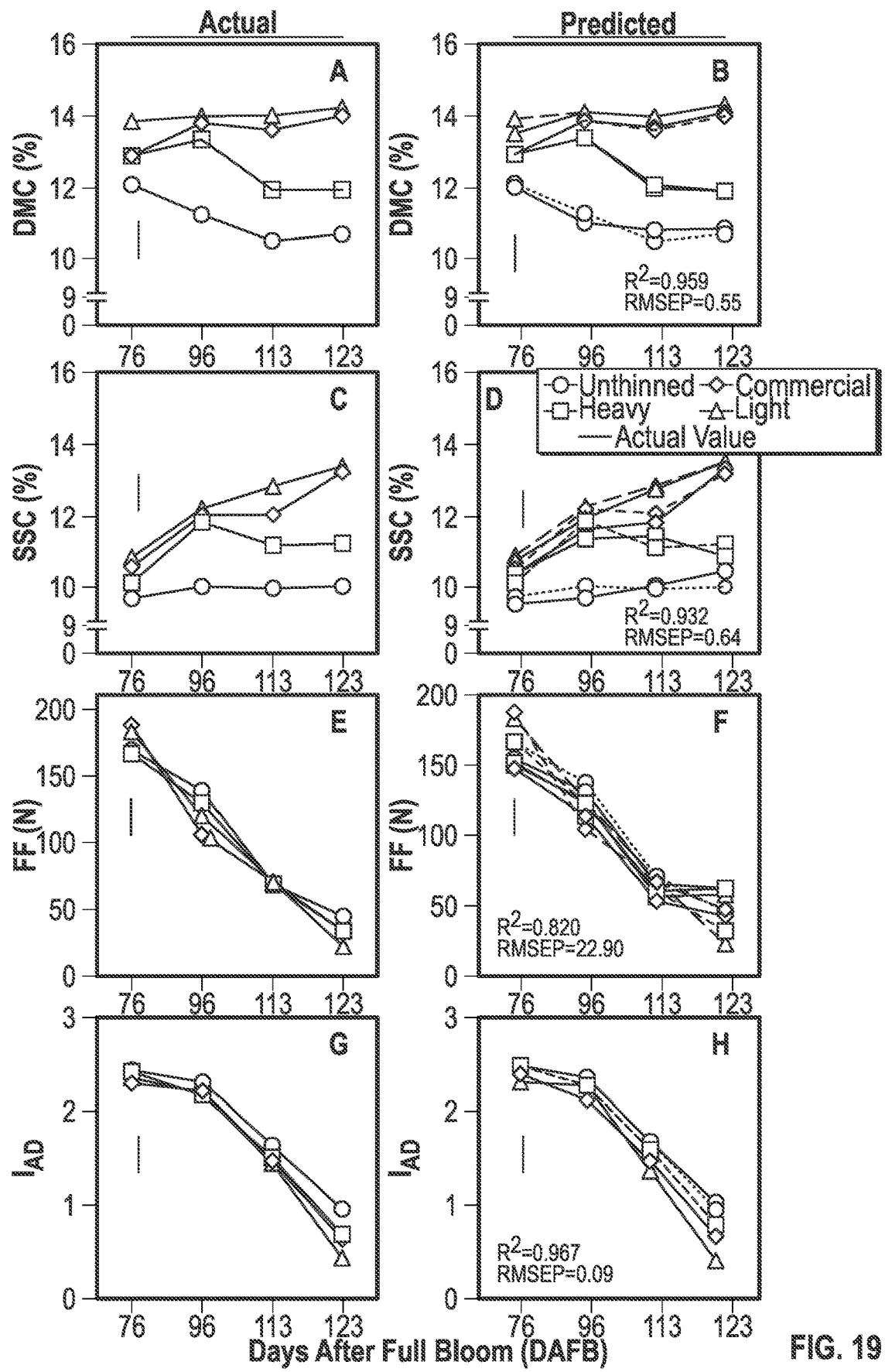
FIG. 19 uses the non-destructive Vis-NIRS regression model to determine the effect of crop load on peach quality and maturity during fruit growth and development.

Relatively high DMC levels (13-14%) were realized early (76 DAFB) across all crop loads tested in peach (FIG. 19, areas A-B). In the commercial and light crop loads, DMC slightly increased towards maturation and harvest. On the other hand, a significant decrease in fruit DMC was observed in unthinned (after 76 DAFB) and heavily cropped trees (after 96 DAFB) during fruit growth and development, and towards maturation (FIG. 19, areas A-B). Soluble solids concentration increased steadily and significantly in commercial and light crop loads during growth and development, whereas SSC slightly increased or remained unaffected in unthinned and heavy crop load trees (FIG. 19, areas C-D). It is important to highlight that both DMC and SSC kinetics during fruit growth and development were similarly captured with both destructive and non-destructive tools.

On the other hand, FF prediction with the combined model (FF/FFm) approach did not provide a sufficient prediction across all developmental stages (RMSEP=22.90). However, prediction of the middle developmental stages (96 and 113 DAFB) was significantly improved (RMSEP=16.83, FIG. 19, area F). Since textural changes can be associated with multiple parameters, these findings might note a limitation in NIRS to accurately predict these changes. Destructive assessment showed that FF loss occurred throughout fruit growth, development and maturation (FIG. 19, area E). Flesh firmness loss did not show significantly different patterns across treatments, except between the commercial and light crop load fruit that were significantly softer than unthinned fruit at 96 and 123 DAFB (harvest).

Index of absorbance difference values were predicted accurately with the developed models and significantly dropped only after 96 DAFB (stage S2) across all treatments, with no differences in $I_{AD}$ loss per day among treatments (FIG. 19, areas G-H). During the last month, prior to harvest (early stage S3), 'Sierra Rich' fruit, across all crop loads, were losing 0.025 to 0.028 $I_{AD}$ value per day, with commercial and light crop loads losing more (i.e., maturing faster), while unthinned and heavy crop loads were losing less (i.e., maturing slower). Ten days prior to harvest (late stage S3), as fruit maturation was advancing, 'Sierra Rich' fruit from the different crop load treatments were losing $I_{AD}$ values with significantly different rates per day. Unthinned trees were losing 0.067, heavy crop load 0.080, commercial crop load 0.083 and light crop load 0.101 of $I_{AD}$ value per day. Based on these differences the effect of crop load in maturation velocity was calculated. Interestingly, the light crop load fruit accelerated fruit maturation by 1.9 days compared to the commercial crop load harvest. On the other hand, heavy crop load and unthinned trees delayed maturation by 1.3 and 4.8 days, respectively, compared to commercial crop load harvest (FIG. 19, areas G-H). These effects of crop load and preharvest conditions on maturation acceleration/delay are further highlighting the practicality of our reliable non-destructive tools to accurately predict an optimal harvest date for improved fruit quality and postharvest handling.

Figure 20A:
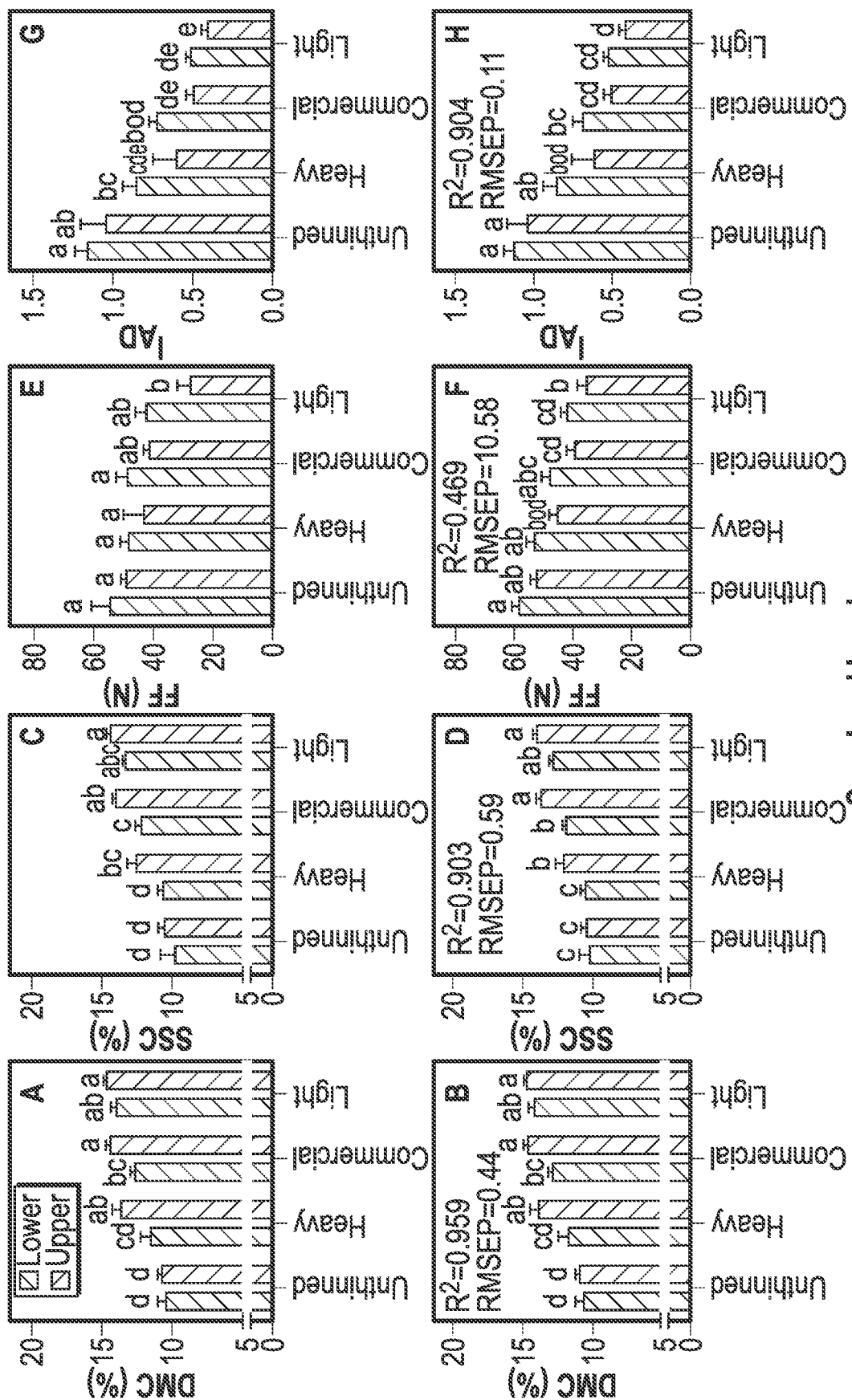
FIGS. 20A-B uses the non-destructive Vis-NIRS regression model to characterize the effect of crop load and fruit position in the canopy on 'Sierra Rich' peach maturity and internal quality at harvest.
Figure 20B:
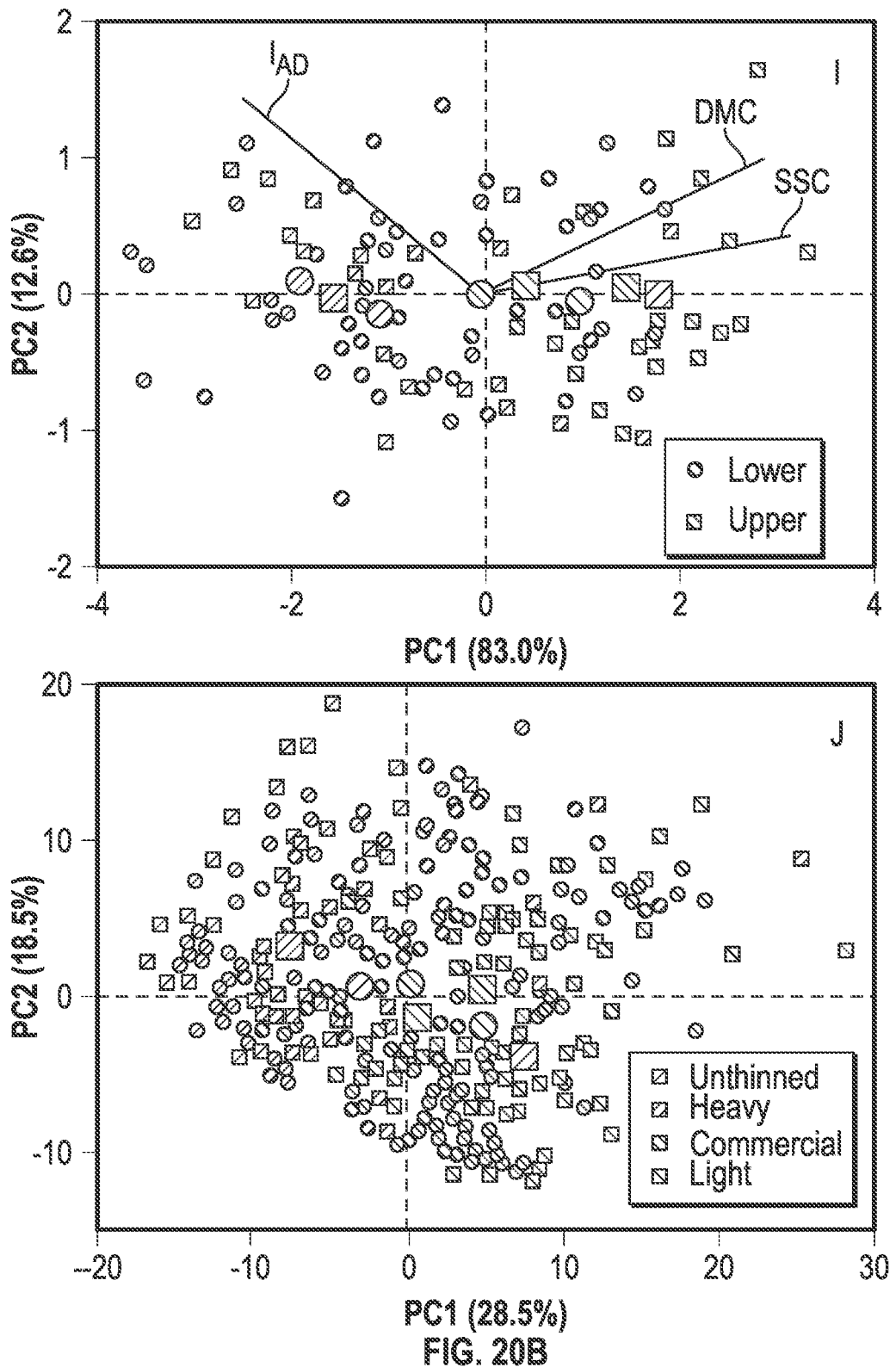

Lastly, the developed non-destructive technology was used for a large-scale assessment of the influence of crop load and fruit position in the canopy on peach fruit internal quality and maturity at harvest (FIGS. 20A-B). Upper canopies across all crop load treatments gave more fruit and higher yields per tree, as shown in Table 5 below:

| Crop load | Fruit (no. · tree$^{-1}$) | Yield (kg · tree$^{-1}$) |
| --- | --- | --- |
| Unthinned upper | 232.7 ± 22.6$^a$ | 22.0 ± 3.7$^a$ |
| Unthinned lower | 147.0 ± 23.7$^b$ | 10.7 ± 1.0$^{bc}$ |
| Heavy upper | 99.3 ± 21.3$^c$ | 13.7 ± 2.1$^b$ |
| Heavy lower | 60.0 ± 10.0$^{cd}$ | 8.0 ± 1.1$^{cd}$ |
| Commercial upper | 41.3 ± 4.9$^d$ | 7.5 ± 0.9$^{cde}$ |
| Commercial lower | 24.3 ± 0.3$^d$ | 4.3 ± 0.0$^{de}$ |
| Light upper | 20.7 ± 8.7$^d$ | 3.9 ± 1.6$^{de}$ |
| Light lower | 11.7 ± 1.2$^d$ | 2.2 ± 0.4$^e$ |

Canopy position did not affect fruit fresh weight and size at harvest in any crop load treatment (FIGS. 20A-B). Interestingly, destructive (actual values, FIG. 20A A, C & G) as well as non-destructive (predicted values, FIG. 20A, areas B, D & H) assessment showed that fruit coming from the upper canopy had higher levels of DMC, SSC and were more mature (reduced $I_{AD}$ values) compared to fruit coming from the lower canopy in the moderate crop load treatments (heavy and commercial). Whereas this was not the case in the extremely heavy (unthinned trees) and light crop load scenarios where the canopy position had no effect on fruit internal quality and maturity ($I_{AD}$) (FIG. 20A). Similarly with what previously reported in the present study DMC ($R^2$=0.96 and RMSEP=0.44, FIG. 20A, area B), SSC ($R^2$=0.90 and RMSEP=0.59, FIG. 20A, area D), and $I_{AD}$ ($R^2$=0.90 and RMSEP=0.11, FIG. 20A, area H) predicted accurately in the fruit coming from the distinct canopy positions across the different crop load treatments with the created models. Contrary, to these models FF prediction in the same fruit with the developed FFm approach was insufficient ($R^2$=0.47, RMSEP=10.58, FIG. 20A, area F).

The full set of predicted DMC, SSC and $I_{AD}$ values (FIG. 20B, area I) as well as the full spectral data (400-1100 mm of second derivative of absorbance, FIG. 20B, area J) were subjected to principal component analysis (PCA) for an overview of data dispersion across the different crop load treatments and canopy positions. Following, both approaches data were sparse mainly in the first principal component (PC1, 83% and 28.5% of variance for predicted values and spectral data, respectively, FIG. 20B, areas I-J), which separates fruit coming from the different canopy positions in heavy and commercial crop loads. Additionally, commercial and light crop loads (regardless of canopy position) were distinct from the unthinned trees (FIG. 20B, areas I-J).

The effect of crop load and canopy position on fruit physiological maturity at harvest was better described with the non-destructive Vis-NIRS spectroscopy and the $I_{AD}$ than the standard destructive FF values (FIG. 20A, areas E & G). This maturity index ($I_{AD}$) can efficiently identify physiological changes occurring during ripening, but it does not correlate with any other means of traditional methodology that determines fruit quality and maturity. More research data are necessary to establish maturity thresholds for different cultivars and types of postharvest handling for the adoption of this index in commercial practice.

Figure 21:
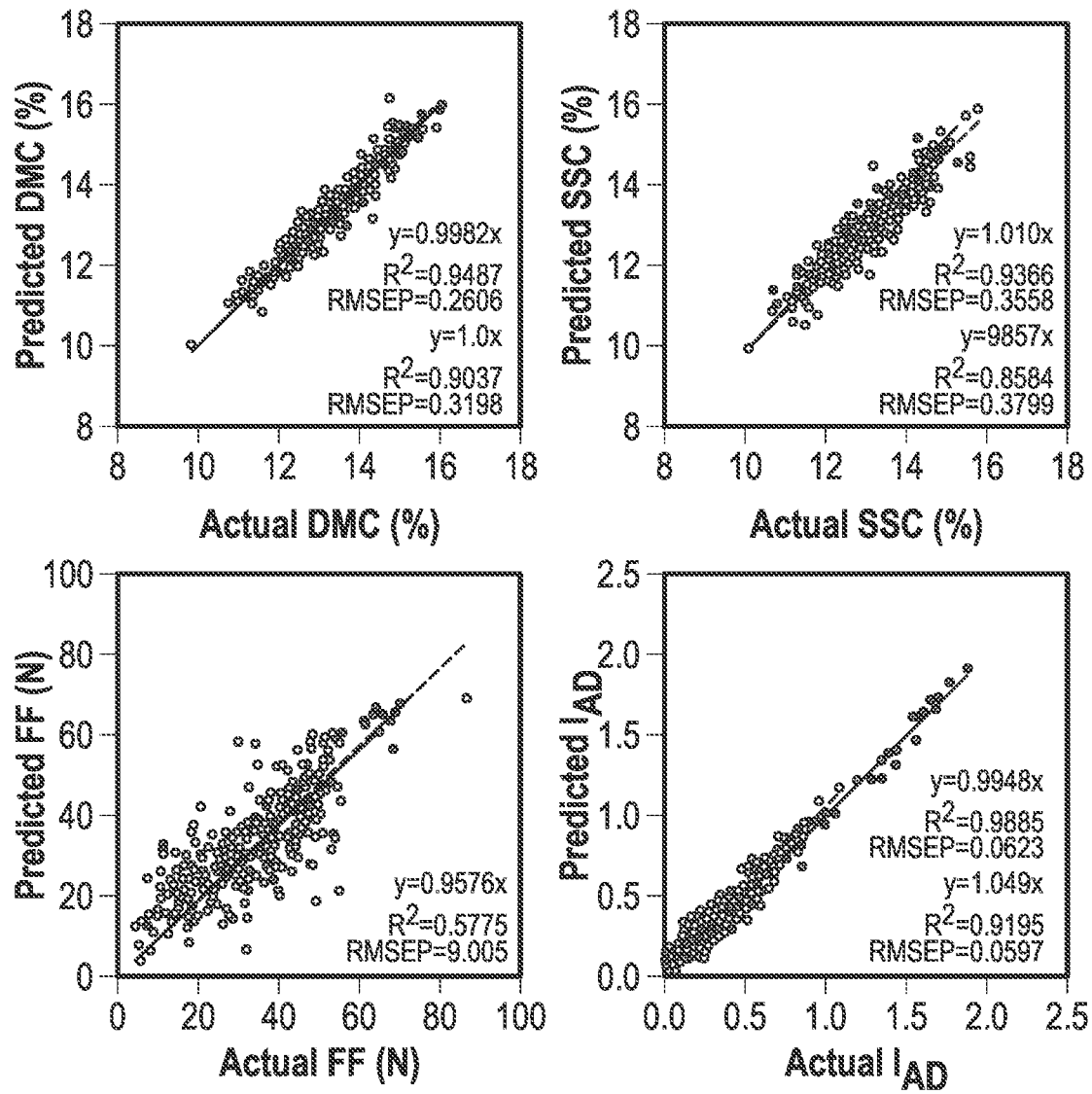
FIG. 21 validates a non-destructive Vis-NIRS regression independent model to by comparing predicted values from the model in the lab with data taken in the field at harvest for the 'Redhaven' cultivar.
Figure 22:
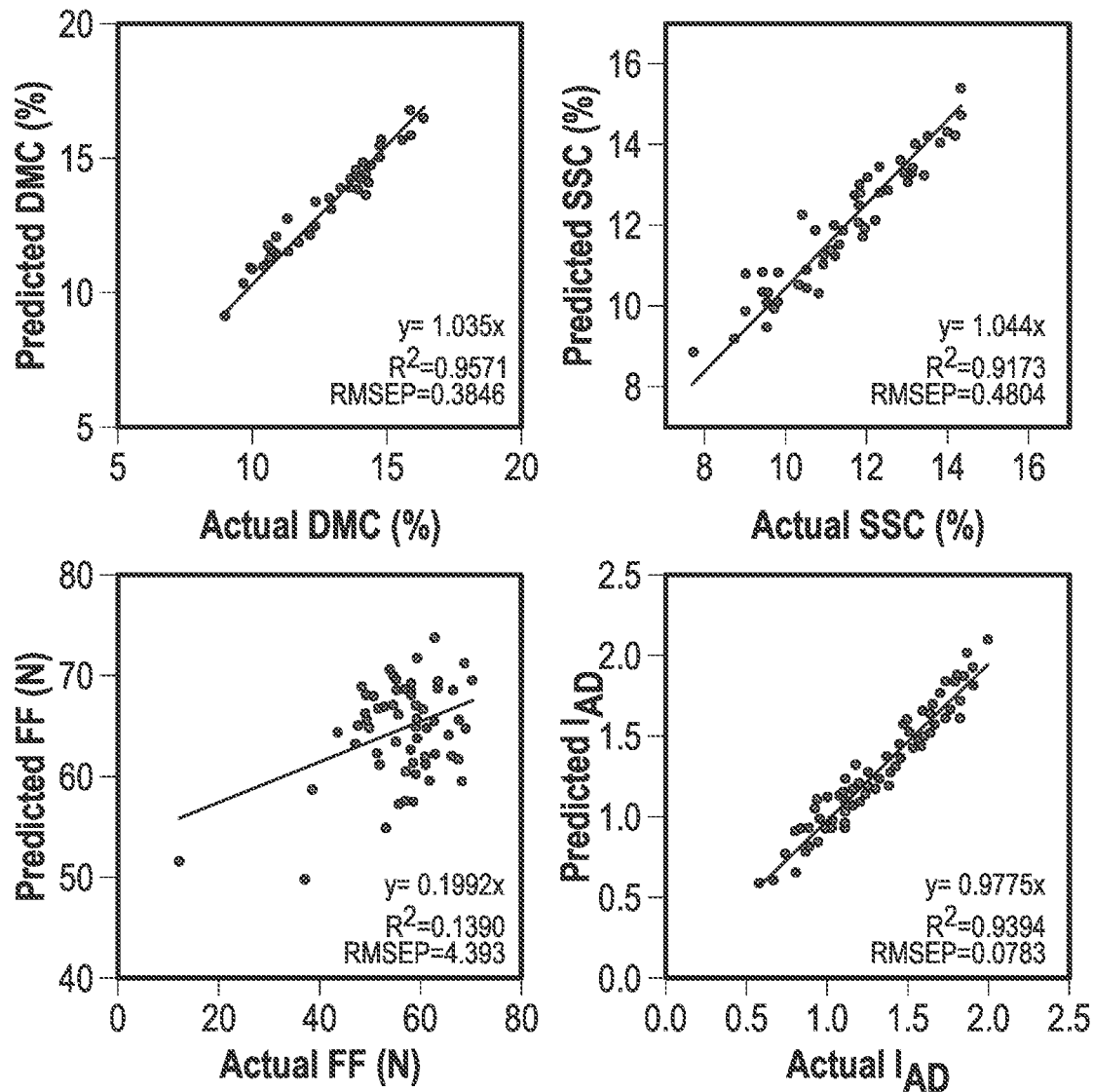
FIG. 22 validates a non-destructive Vis-NIRS regression independent model to by comparing predicted values from the model in the lab with data taken in the field at harvest for the 'Cresthaven' cultivar.
Figure 23A:
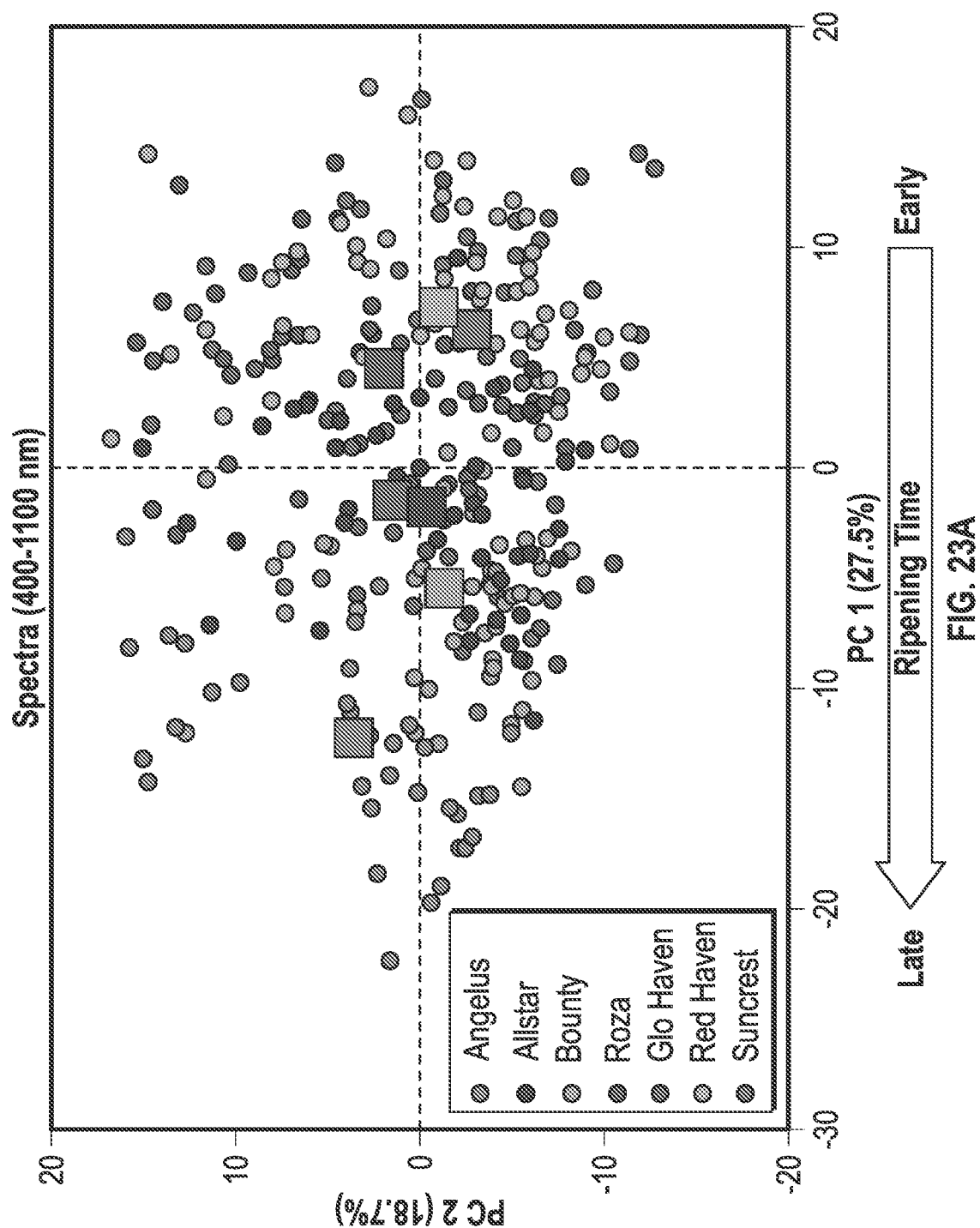
FIGS. 23A-C validates developed models of the implemented device show strong performance for various other peach cultivars.
Figure 23B:
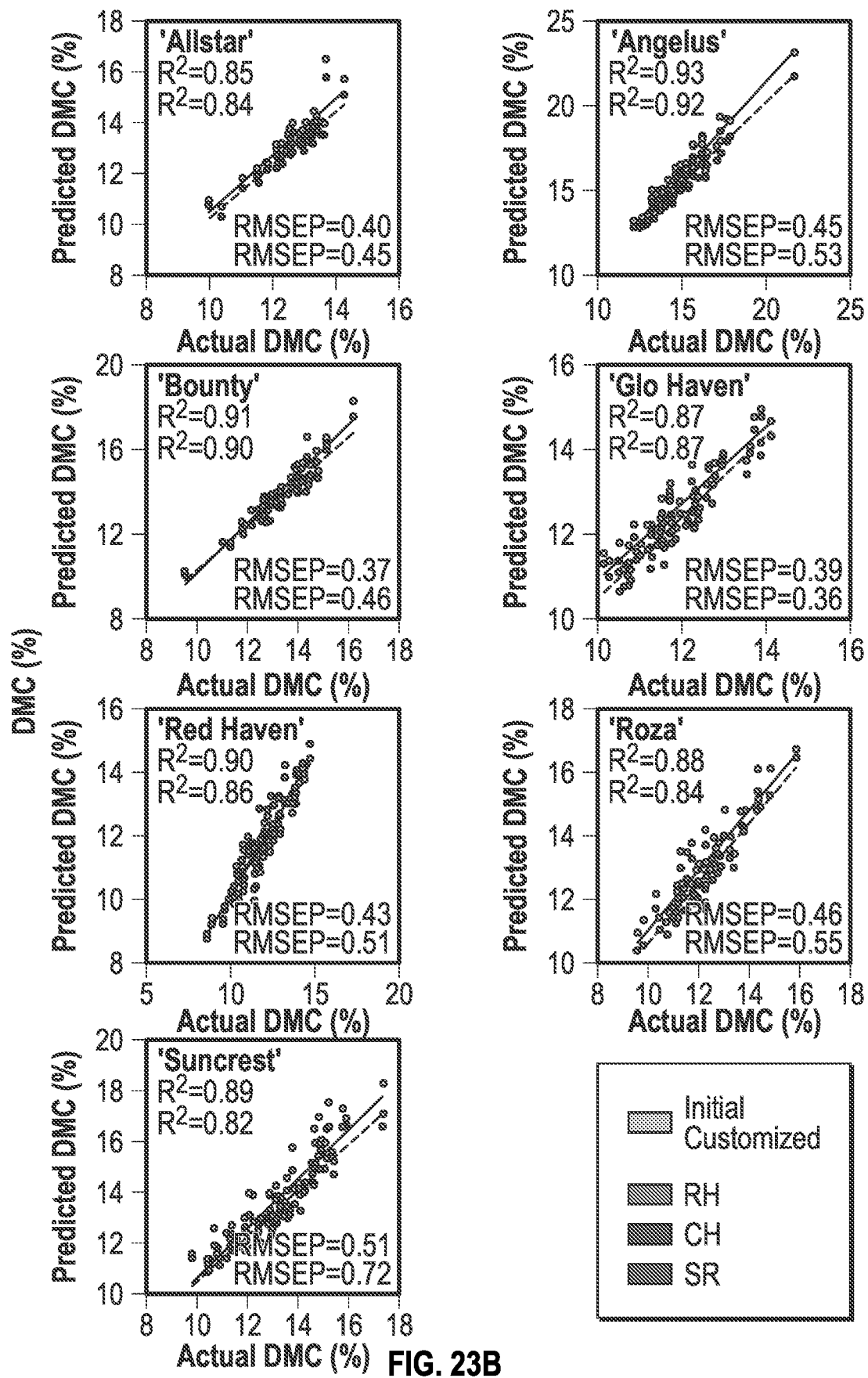
Figure 23C:
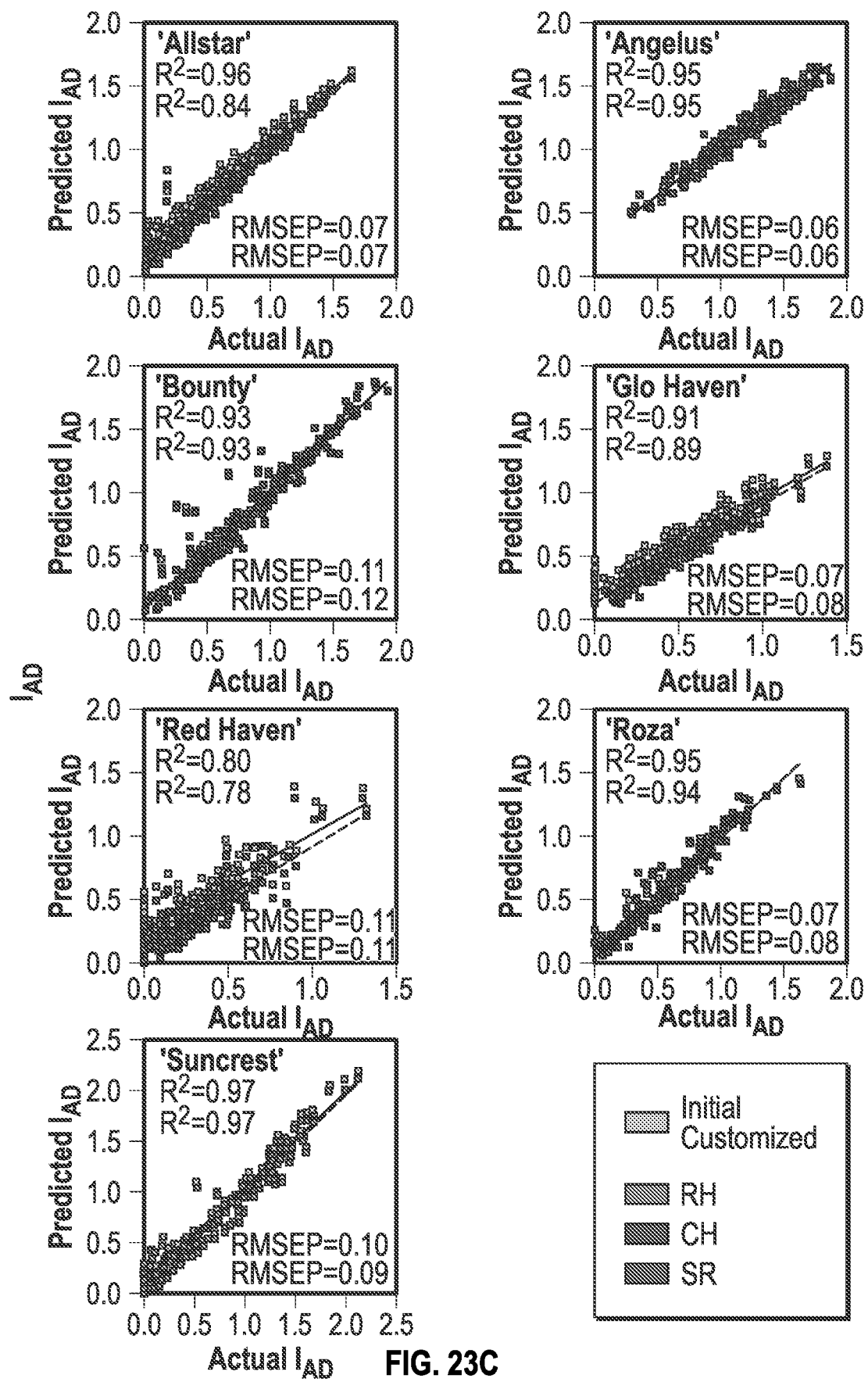

Following exactly the same protocol accurate non-destructive multivariate regression models were developed for fruit maturity and internal quality assessment in an early ripening bi-colored peach cultivar ('Redhaven') and a late ripening bi-colored cultivar 'Cresthaven'. These two cultivars and the variation included in the developed models covers a broad range of fruit typologies across yellow fleshed peaches and allows for further customization and creation of cultivar-specific models that can similarly and accurately assess fruit maturity and internal quality with a single scan, as shown in FIGS. 21-22. FIGS. 23A-C show developed models of the implemented device correlate strong performance with respect to at least seven peach cultivars, including Allstar, Angelus, Bounty, Glo Haven, Red Haven, Roza, and Suncrest. In the aggregated plot of FIG. 23A, the cultivars are segregated from right (early) to left (late) in order of ripening time.

CONCLUSION

From the foregoing, it can be seen that the present invention accomplishes at least all of the stated objectives.

With greater particularity, crop load management substantially affects peach fruit internal quality and maturation processes during fruit growth and development, allowing for the calibration of accurate regression models. Through a crop load×fruit developmental stage calibration approach, NIRS can accurately and efficiently sense DMC and SSC differences in peaches using handheld sensors. Peach DMC shows a strong correlation with SSC and can be used as a more accurate non-destructive indicator of peach fruit internal quality and sugar content. FF is poorly predicted through Vis-NIRS spectra acquisition, while $I_{AD}$ is successfully predicted with the same instrumentation set-up. Index of absorbance difference does not correlate with FF, but better describes fruit physiological maturity status.

Large-scale field evaluation shows heavier crop loads reduce peach quality and delayed maturity, upper canopy position advanced both, while extensive tree vigor as affected by cultivar or rootstock is detrimental for peach internal quality. Rapid assessment of peach quality and maturity with a single scan across a variety of cultivars will provide a new understanding of preharvest factors to improve stone fruit performance and productivity in a changing environment and can enhance Vis-NIRS adaptation across tree fruit supply chain.

These findings contribute to a novel non-destructive sensor setup that accurately and efficiently measures internal fruit quality (DMC, SSC) and maturity ($I_{AD}$) with a single scan.

The proposed sensor was, and can be, used to estimate the effect of crop load and canopy position on peach fruit quality and maturity in the field during fruit growth, development and at harvest. Large-scale and accurate non-destructive analysis quantifies in detail that heavier crop loads reduce DMC and SSC and delayed fruit maturity as measured by $I_{AD}$. On the other hand, upper canopy position can improve fruit internal quality (DMC, SSC) and advanced maturity ($I_{AD}$) mainly in the moderate crop loads.

The non-destructive fruit quality predictive performance of this Vis-NIRS technology is significant and will likely lead to further significant improvements in the commercialization of this technology in the tree fruit industry.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 6

| List of Reference Characters | |
|---|---|
| 100 | time series graph of tracking peach per capita over time |
| 200 | bar graph tracking production of peaches and nectarines over time |
| 300 | peach growth process |
| 400 | environment for optimizing pre-harvest factors |
| 402 | crop load/thinning method/thinning time |
| 404 | fruit canopy position |
| 406 | irrigation system |
| 408 | mineral nutrition/foliar sprays |
| 410 | plant growth regulators |
| 412 | light manipulation/photo-selective nets |
| 414 | canopy architecture |
| 416 | growing climate monitors and/or manipulators |
| 418 | light manipulation/reflectance films |
| 420 | rootstocks |
| 500 | comparative view of quality changes during peach development and ripening on-tree |
| 600 | destructive fruit quality and maturity assessment equipment |
| 700 | open-type produce quality meter |
| 800 | closed-type produce quality meter |
| 900 | method for measuring fruit quality non-destructively |
| 1000 | near infrared radiation |
| 1000A | example comparison between predicted DMC and actual DMC |
| 1000B | example comparison between predicted SSC and actual SSC |
| 1000C | example comparison between predicted FF and actual FF |
| 1000D | example comparison between predicted $I_{AD}$ and actual $I_{AD}$ |
| 1000E | example comparison between actual SSC and actual DMC |
| 1000F | example comparison between flesh firmness and $I_{AD}$ |
| 1100 | example crop loads |
| 1100A | example unthinned corp load |
| 1100B | example heavy crop load |
| 1100C | example commercial crop load |
| 1100D | example light crop load |
| 1200 | effects on various crop loads on peach DMC |
| 1200A | example comparison between frequency of crop load and DMC |
| 1200B | example comparison between predicted DMC and actual DMC |
| 1200C | example correlation between SSC and DMC |
| 1300 | effects on various crop loads on peach SSC |
| 1300A | example comparison between frequency of crop load and SSC |
| 1300B | example comparison between predicted SSC and actual SSC |
| 1300C | example correlation between SSC and DMC |
| 1400 | effects on various crop loads on peach $I_{AD}$ |
| 1400A | example comparison between frequency of crop load and $I_{AD}$ |
| 1400B | example correlation FF and $I_{AD}$ |
| 1500 | example comparison between TCSA and cumulative yield |
| 1600 | effects of rootstock on peach productivity |
| 1600A | example comparison between TCSA and DMC |
| 1600B | example comparison between predicted DMC and actual DMC |
| 1600C | example comparison between actual SSC and actual DMC |

The technology disclosed herein can significantly support growers, shippers, packers and retailers with decisions regarding the proper harvest time and postharvest handling practices. Additionally, this technology can aid researchers with the evaluation of the true impact of orchard factors such as cultural techniques, production systems and new genotypes (cultivars and rootstocks) on peach internal quality to increase consumer satisfaction.

Glossary

Unless defined otherwise, all technical and scientific terms used above have the same meaning as commonly understood by one of ordinary skill in the art to which embodiments of the present invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

The term "canopy" refers to the aboveground portion of a plant cropping or crop, formed by the collection of individual plant crowns.

The term "rootstock" refers to a part of a plant, often an underground part, from which new above-ground growth can be produced.

The term "crop load" is a quantitative parameter that refers to the number of fruit per tree.

The term "cultivar" refers to a plant variety that has been produced in cultivation by selective breeding.

The term "dry matter" in a plant refers to all constituents of a plant material excluding water. The term "dry matter content" is a quantitative parameter that refers to the percentage of dry matter making up the total plant material.

The term "soluble solids" refers to solids that are capable of being dissolved in a solvent, such as water.

The term "mass spectrometry" refers an analytical technique that is used to measure the mass-to-charge ratio of ions.

The term "near infrared spectroscopy" (NIRS) refers to a spectroscopic method that uses the near-infrared region of the electromagnetic spectrum (from 780 nm to 2500 nm).

The term "vigor", with respect to trees, refers to a health and resilience of a tree, reflected in the capacity of the whole tree to grow. Vigor can also be described as the capacity to survive under increasing stimulate that threaten survival. The term "tree vigor" can sometimes be quantified as the ratio of the annual growth of wood on the stem per unit of leaf area.

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

The present disclosure is further defined by the following numbered paragraphs:

1. A method for accurately and non-destructively predicting crop maturity and quality comprising:
   taking an infrared (IR) scan using visual light radiation and near infrared spectroscopy (Vis-NIRS) to detect several quantitative parameters at one time;
   using a multivariate Vis-NIRS-based prediction model to simultaneously evaluate internal quality and a physiological maturity of a crop based upon the detected quantitative parameters.

2. The method of paragraph 1 where the crop is a fruit.

3. The method of paragraph 2 wherein the fruit is from a *Prunus* species.

4. The method of paragraph 3 wherein the *Prunus* species is a peach.

5. The method of any one of paragraphs 1-4 wherein the taking of the IR scan using near infrared spectroscopy is accomplished with a handheld sensor.

6. The method of any one of paragraphs 1-5 wherein the multivariate Vis-NIRS-based prediction models are based on a crop load and developmental stage calibration approach.

7. The method of any one of paragraphs 1-6 wherein the quantitative parameters are selected from the group consisting of a dry matter content (DMC), a soluble solids concentration (SCC), and an index of absorbance difference ($I_{AD}$).

8. The method of any one of paragraphs 1-7 wherein the multivariate Vis-NIRS-based model is based on a predicted value selected from said group of quantitative parameters.

9. The method of any one of paragraphs 1-8 wherein the multivariate Vis-NIRS-based prediction model is calibrated on-site by multiplying the crop load by a fruit developmental stage protocol.

10. The method of any one of paragraphs 1-9 wherein the multivariate Vis-NIRS-based prediction model is calibrated at a factory using an index of absorbance difference ($I_{AD}$).

11. The method of any one of paragraphs 1-10 further comprising altering an amount of irrigation time or an amount of water applied to the crop based upon the IR scan and the multivariate Vis-NIRS-based prediction model.

12. The method of any one of paragraphs 1-11 further comprising using a foliar spray to address a nutrient deficiency in the crop based upon the IR scan and the multivariate Vis-NIRS-based prediction model.

13. The method of any one of paragraphs 1-12 further comprising regulating a growth of the crop based upon the IR scan and the multivariate Vis-NIRS-based prediction model.

14. The method of any one of paragraphs 1-13 further comprising manipulating an amount of light to the crop based upon the IR scan and the multivariate Vis-NIRS-based prediction model.

15. The method of any one of paragraphs 1-14 further comprising altering a growing climate of the crop based upon the IR scan and the multivariate Vis-NIRS-based prediction model.

16. The method of any one of paragraphs 1-15 using rootstock to stabilize the crop based upon the IR scan and the multivariate Vis-NIRS-based prediction model.

17. The method of any one of paragraphs 1-16 changing a canopy architecture of the crop based upon the IR scan and the multivariate Vis-NIRS-based prediction model.

18. The method of any one of paragraphs 1-17 further comprising thinning a crop load based upon the IR scan and the multivariate Vis-NIRS-based prediction model.

19. The method of any one of paragraphs 1-18 further comprising selecting an optimal time to harvest the crop based upon the IR scan and the multivariate Vis-NIRS-based prediction model.

20. A spectrometer comprising:
a non-destructive sensor capable of accurately measuring or estimating with a single infrared (IR) scan two or more quantitative parameters selected from the group consisting of:
(a) a dry matter content;
(b) a soluble solids content;
(c) an index of absorbance difference ($I_{AD}$); and
(d) an internal physical characteristic;
for one or more fruits of a tree;
a computer processing unit (CPU) capable of carrying out an algorithm that automatically predicts an overall quality and a maturity of the one or more fruits by converting the two or more quantitative parameters to a single prediction value.

21. The spectrometer of paragraph 20 wherein the internal physical characteristic relates to a firmness.

22. The spectrometer of any one of paragraphs 21-22 wherein the non-destructive sensor is able to detect an effect of crop load and canopy position of the one or more fruits.

23. The spectrometer of any one of paragraphs 21-22 wherein the algorithm can predict said effect based upon the one or more quantitative parameters.

24. The spectrometer of any one of paragraphs 21-23 wherein the spectrometer was calibrated with fruit coming from various crop loads and at different fruit developmental stage following a crop load×development.

25. A controllable growing environment for a fruit tree comprising:
the spectrometer according to any one of paragraphs 20-24;
growth regulators comprising:
an irrigation system; and means for delivering nutrients to the one or more fruits;
wherein the growth regulators are automatically controlled by commands produced in response to carrying out said algorithm.

26. The controllable growing environment of paragraph 25 wherein the growth regulators further comprise an artificial sunlight source and/or means for manipulating an amount of sunlight to the fruit.

27. The controllable environment of any one of paragraphs 25-26 wherein the growth regulators further comprise an air quality monitor or a thermostat.

28. The controllable environment of any one of paragraphs 25-27 further comprising a rootstock to stabilize the tree.

29. The controllable environment of any one of paragraphs 25-28 further comprising a means for measuring tree vigor.

30. The controllable environment of any one of paragraphs 25-29 further comprising an automated agricultural implement capable of harvesting fruits at an optimal time determined and/or suggested by said algorithm.

What is claimed is:

1. A method for accurately and non-destructively predicting crop maturity and quality comprising:
taking an infrared (IR) scan using visual light radiation and near infrared spectroscopy (Vis-NIRS) to detect two or more quantitative parameters at one time, wherein the two or more quantitative parameters are selected from the group consisting of:
a dry matter content (DMC), a soluble solids concentration (SSC), and an index of absorbance difference (IAD);
using a multivariate Vis-NIRS-based prediction model to simultaneously evaluate internal quality and a physiological maturity of a crop based upon the detected quantitative parameters.

2. The method of claim 1 where the crop is a fruit.

3. The method of claim 2 wherein the fruit is from a *Prunus* species.

4. The method of claim 3 wherein the *Prunus* species is a peach.

5. The method of claim 1 wherein the taking of the IR scan is accomplished with a handheld sensor.

6. The method of claim 1 wherein the multivariate Vis-NIRS-based prediction model is calibrated based on various crop loads and various developmental stages of the crop.

7. The method of claim 1 wherein the multivariate Vis-NIRS-based model is based on a predicted value selected from said group of quantitative parameters.

8. The method of claim 1 wherein the multivariate Vis-NIRS-based prediction model is calibrated at a factory using an index of absorbance difference ($I_{AD}$).

9. The method of claim 1 further comprising:
(a) altering an amount of irrigation time or an amount of water applied to the crop;
(b) using a foliar spray to address a nutrient deficiency in the crop;
(c) regulating a growth of the crop;
(d) manipulating an amount of light to the crop;
(e) altering a growing climate of the crop;
(f) using a rootstock to stabilize the crop; and/or
(g) changing a canopy architecture of the crop;
based upon the scan and the multivariate Vis-NIRS-based prediction model.

10. A method for accurately and non-destructively predicting crop maturity and quality comprising:
taking an infrared (IR) scan using visual light radiation and near infrared spectroscopy (Vis-NIRS) to detect two or more quantitative parameters at one time;
using a multivariate Vis-NIRS-based prediction model to simultaneously evaluate internal quality and a physiological maturity of a crop based upon the detected quantitative parameters;
wherein the multivariate Vis-NIRS-based prediction models are based on a crop load and developmental stage calibration approach;
wherein the quantitative parameters are selected from the group consisting of a dry matter content (DMC), a soluble solids concentration (SCC), and an index of absorbance difference ($I_{AD}$);
wherein the multivariate Vis-NIRS-based prediction model is calibrated on-site by multiplying the crop load by a number associated with a fruit developmental stage protocol.

11. A spectrometer comprising:
a non-destructive sensor capable of accurately measuring or estimating with a single infrared (IR) scan two or more quantitative parameters selected from the group consisting of:
(a) a dry matter content;
(b) a soluble solids content;
(c) an index of absorbance difference ($I_{AD}$); and
(d) a flesh firmness;
for one or more fruits of a tree;
a computer processing unit (CPU) capable of carrying out an algorithm that automatically predicts an overall quality and a maturity of the one or more fruits by converting the two or more quantitative parameters to a single prediction value.

12. The spectrometer of claim 11 wherein the nondestructive sensor is able to detect an effect of crop load and canopy position of the one or more fruits.

13. The spectrometer of claim 12 wherein the algorithm can predict said effect based upon the one or more quantitative parameters.

14. The spectrometer of claim 11 wherein the spectrometer was calibrated with fruit coming from various crop loads and at different fruit developmental stages.

15. A controllable growing environment for a fruit tree comprising:
   the spectrometer of claim 11;
   growth regulators comprising:
      an irrigation system; and
      means for delivering nutrients to the one or more fruits;
   wherein the growth regulators are automatically controlled by commands produced in response to carrying out said algorithm.

16. The controllable growing environment of claim 15 wherein the growth regulators further comprise an artificial sunlight source and/or means for manipulating an amount of sunlight to the fruit.

17. The controllable growing environment of claim 15 wherein the growth regulators further comprise an air quality monitor or a thermostat.

18. The controllable growing environment of claim 15 further comprising a rootstock to stabilize the tree.

* * * * *